United States Patent
Witney et al.

(10) Patent No.: US 10,039,844 B2
(45) Date of Patent: Aug. 7, 2018

(54) IMAGING TUMOR GLYCOLYSIS BY NON-INVASIVE MEASUREMENT OF PYRUVATE KINASE M2

(71) Applicant: The Board of Trustees of the Leland Stanford Junior University, Palo Alto, CA (US)

(72) Inventors: Timothy Witney, Denton (GB); Michelle L. James, Menlo Park, CA (US); Sanjiv S. Gambhir, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 482 days.

(21) Appl. No.: 14/956,431

(22) Filed: Dec. 2, 2015

(65) Prior Publication Data
US 2016/0158389 A1 Jun. 9, 2016

Related U.S. Application Data

(60) Provisional application No. 62/086,944, filed on Dec. 3, 2014.

(51) Int. Cl.
| | | |
|---|---|---|
| A61K 51/00 | (2006.01) | |
| A61M 36/14 | (2006.01) | |
| A61K 51/04 | (2006.01) | |
| C07D 295/26 | (2006.01) | |
| G01N 33/574 | (2006.01) | |
| G01N 33/60 | (2006.01) | |

(52) U.S. Cl.
CPC ........ A61K 51/0459 (2013.01); C07D 295/26 (2013.01); G01N 33/57496 (2013.01); G01N 33/60 (2013.01); G01N 2333/91215 (2013.01)

(58) Field of Classification Search
CPC ............. A61K 51/0459; C07D 295/26; G01N 33/57496; G01N 33/60; G01N 2333/91215
USPC ....................................................... 424/1.89
See application file for complete search history.

(56) References Cited

U.S. PATENT DOCUMENTS

| | | | | |
|---|---|---|---|---|
| 2008/0294289 | A1* | 11/2008 | Lim .............................. | 700/268 |
| 2010/0056533 | A1* | 3/2010 | Ametamey et al. .......... | 514/249 |
| 2012/0108631 | A1* | 5/2012 | Becker et al. ................ | 514/312 |

OTHER PUBLICATIONS

Zhang et al. Curr. Top. Med. Chem. 2007,7,1817-1828.*
Halldin et al. Curr. Pharm. Des., 2001, 7, 1907-1929.*
Gao et al. Appl. Rad. Isot. 70 (2012) 1558-1563.*
Wong et al. Int. J. Cell Biol. 2013, 1-11.*
Boxer et al. J. Med. Chem. 2010, S1-S25.*
Boxer, MB et al. Evaluation of Substituted N,N0-Diarylsulfonamides as Activators of the Tumor Cell Specific M2 Isoform of Pyruvate Kinase, J. Med. Chem. 2010, 53, 1048-1055.
Vander Heiden, MG et al. Understanding the Warburg Effect: The Metabolic Requirements of Cell Proliferation. Science. May 22, 2009; 324(5930): 1029-1033.
Vander Heiden, MG et al. Identification of small molecule inhibitors of pyruvate kinase M2. Biochemical Pharmacology 79 (2010) 1118-1124.
Vander Heiden, MG et al. Evidence for an alternative glycolytic pathway in rapidly proliferating cells. Science. Sep. 17, 2010; 329(5998): 1492-1499.
Neves AA, Brindle KM. Assessing Responses to Cancer Therapy using Molecular Imaging. Biochimica et Biophysica Acta 1766 (2006) 242-261.
Challapalli A and Aboagye EO. Positron Emission Tomography Imaging of Tumor Cell Metabolism and Application to Therapy Response Monitoring. Frontiers in Oncology. Feb. 2016, vol. 6, Article 44.

* cited by examiner

*Primary Examiner* — Michael G Hartley
*Assistant Examiner* — Sean R Donohue
(74) *Attorney, Agent, or Firm* — Thomas | Horstemeyer, LLP

(57) ABSTRACT

A novel pyruvate kinase M2 (PKM2)-specific activator, [$^{11}$C]DASA-23 and derivatives thereof, and methods for their rapid synthesis are provided. The probes are particularly useful in methods for the non-invasive positron emission tomography (PET) detection and imaging of PKM2 expression in subcutaneous and orthotopic tumors. [$^{11}$C] DASA-23 cell uptake correlates with PKM2 protein expression in cultured tumor cells and orthotopic tumors are delineated from the surrounding normal brain tissue in vivo.

14 Claims, 16 Drawing Sheets

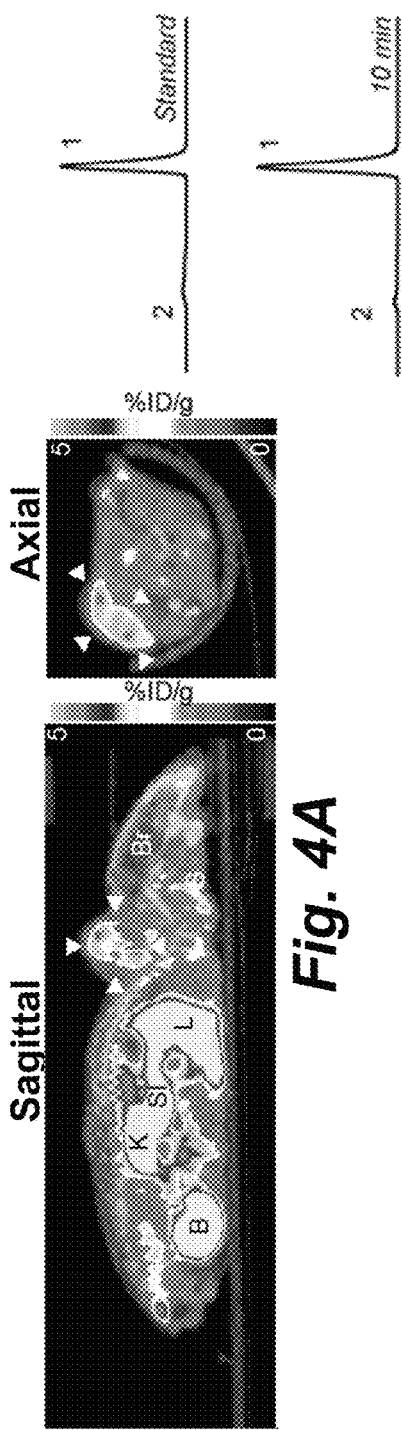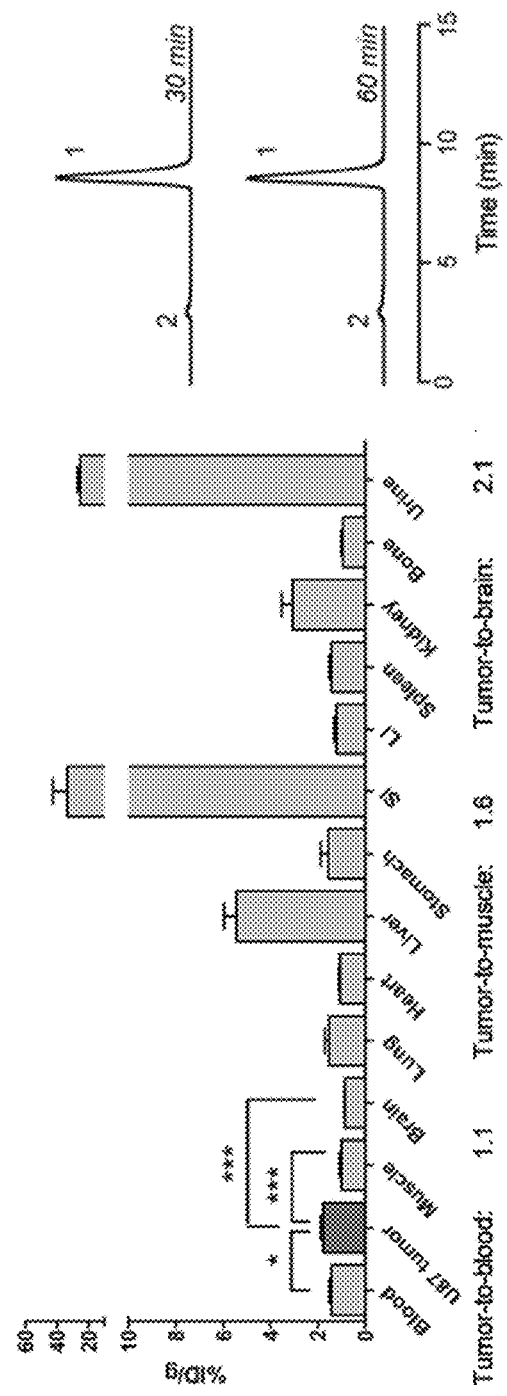
Fig. 4A
Fig. 4B
Fig. 4C

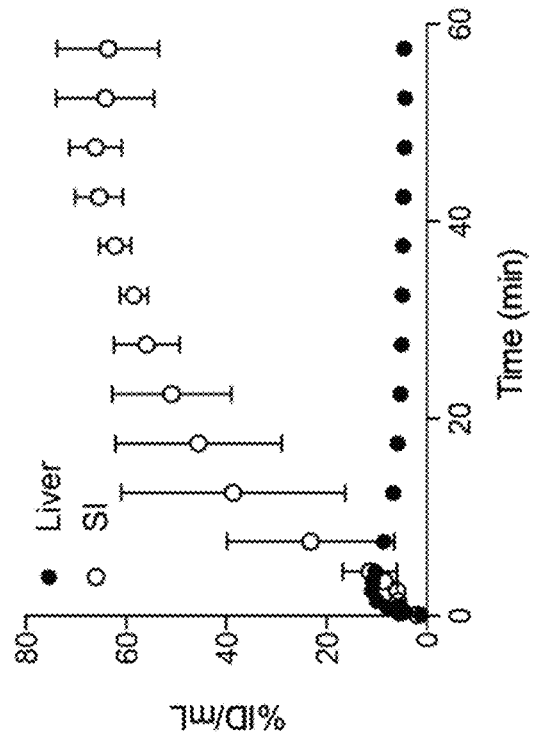
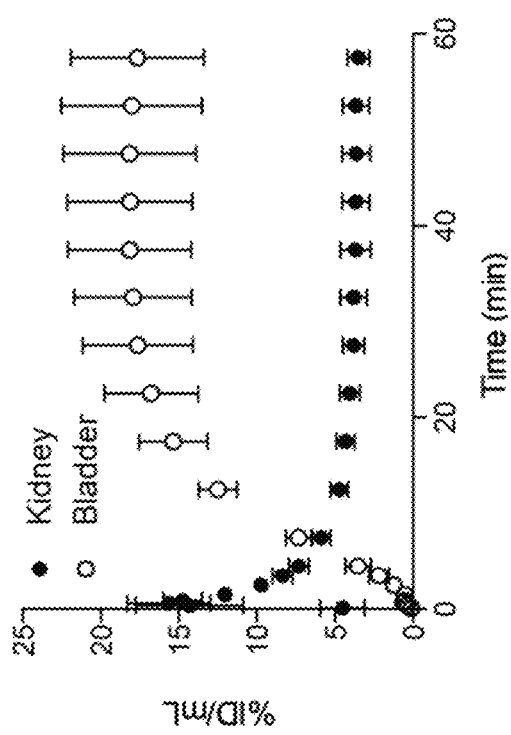
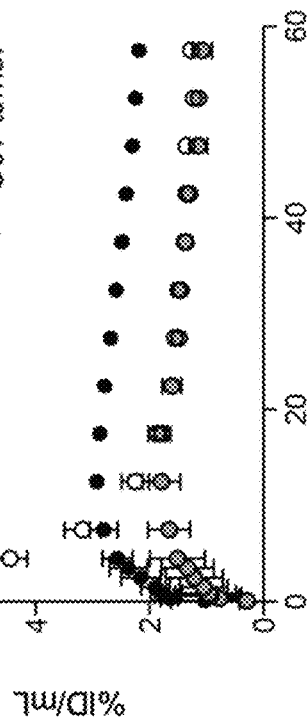
Fig. 5A
Fig. 5B
Fig. 5C

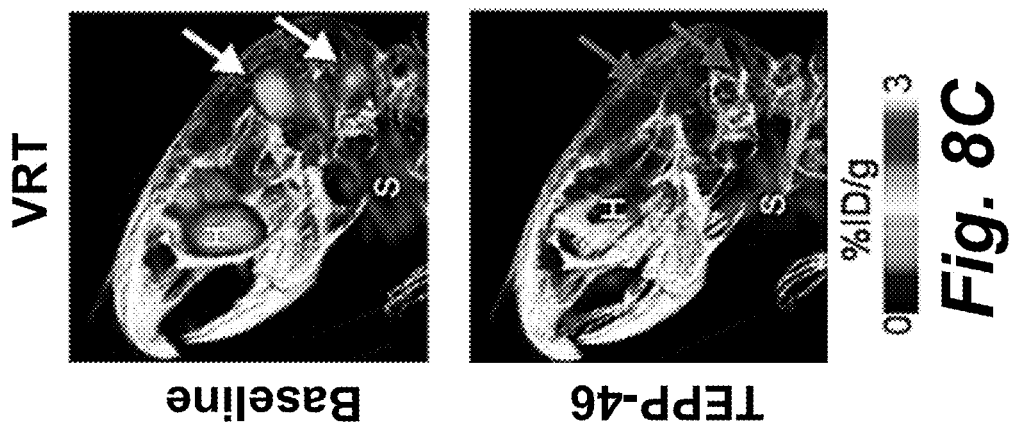
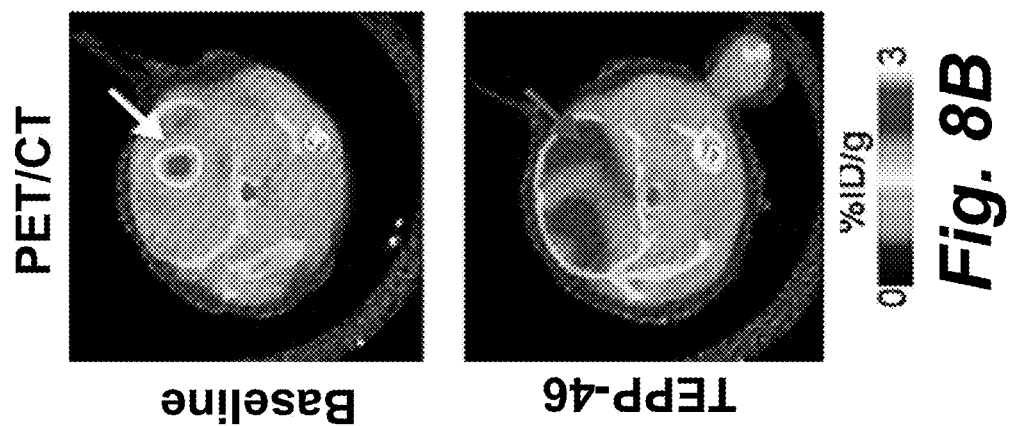
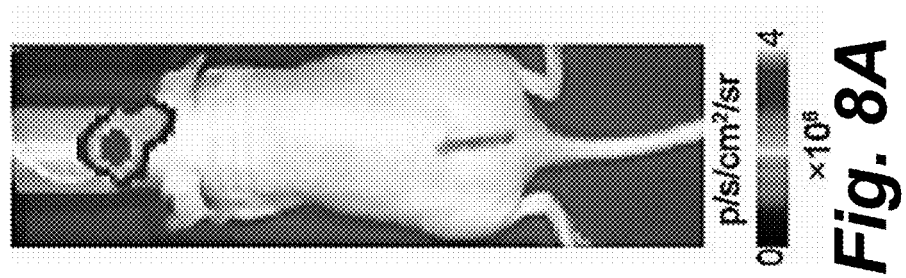

Scheme A

Scheme B

Scheme C

IMAGING TUMOR GLYCOLYSIS BY NON-INVASIVE MEASUREMENT OF PYRUVATE KINASE M2

CROSS REFERENCE TO RELATED APPLICATIONS

This application claims priority benefit of U.S. Provisional Patent Application Ser. No. 62/086,944 filed on Dec. 3, 2014 and titled "IMAGING TUMOR GLYCOLYSIS DOWNSTREAM OF HEXOKINASE THROUGH NON-INVASIVE MEASUREMENT OF PYRUVATE KINASE M2" the entire disclosure of which is herein incorporated by reference in its entirety.

STATEMENT REGARDING FEDERALLY SPONSORED RESEARCH OR DEVELOPMENT

This invention was made with Government support under contracts 1P50CA114747-06 and CA124435-02 awarded by the National Institutes of Health. The Government has certain rights in this invention.

TECHNICAL FIELD OF THE DISCLOSURE

The present disclosure is generally related to probes and methods advantageous for detecting pyruvate kinase M2 in cells. The present disclosure is further generally related to methods of imaging tumors by detecting pyruvate kinase M2 activity using positron emission tomography (PET)-specific probes.

SEQUENCE LISTING

The present disclosure includes a sequence listing incorporated herein by reference in its entirety.

BACKGROUND

Tumors undergo metabolic reprogramming to support the synthesis of new macromolecules required for rapid cell division, additionally providing a selective advantage for progression and protection from death (Cairns et al., (2011) *Nature Revs. Cancer* 11: 85-95). The concept of metabolic adaptation in tumors was first described by Otto Warburg in the 1920s following the discovery that cancer cells display increased rates of glucose utilization in comparison to normal tissue, even under aerobic conditions (Warburg O. (1956) *Science* 123: 309-314). It is now known that the metabolic transformation of cancer cells encompasses multiple interconnecting metabolic networks (Carracedo et al., (2013) *Nature Revs. Cancer* 13: 227-232), with feedback loops and crosstalk acting to provide plasticity for cells to survive the steep and localized nutrient and oxygen gradients in the harsh tumor microenvironment (Gatenby & Gillies (2004) *Nature Revs. Cancer* 4: 891-899). Central to tumor metabolism is the glycolytic pathway that sustains tumors by generating ATP and by synthesizing intermediates for biosynthetic pathways.

SUMMARY

Cancer cells reprogram their metabolism to meet increased biosynthetic demands, commensurate with elevated rates of replication. Aberrant tumor glycolysis has long been known to support the synthesis of metabolic precursors required to sustain this anabolic phenotype. Pyruvate kinase catalyzes the final and rate-limiting step in glycolysis, with the M2 spliced isoform (PKM2) as a key regulator of aerobic glycolysis in tumors. The present disclosure encompasses embodiments of a non-invasive detection of PKM2 expression in subcutaneous and orthotopic tumors through positron emission tomography (PET) imaging of the PKM2 activator, [$^{11}$C]DASA-23. [$^{11}$C]DASA-23 cell uptake correlates with PKM2 protein expression in cultured tumor cells and orthotopic tumors are delineated from the surrounding normal brain tissue in vivo. PET/MR imaging confirmed correspondence of the [$^{11}$C]DASA-23 signal with the location of intracranial tumors, further confirmed ex vivo by histopathology and exclusive tumor-associated PKM2 expression. Together, these data provide the basis for imaging agents that target this important gatekeeper of tumor glycolysis.

The present disclosure provides embodiments of a pharmaceutically acceptable probe composition comprising a Positron Emission Tomography (PET)-detectable radiolabelled probe having the formula:

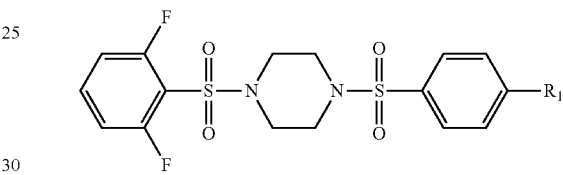

wherein $R_1$ can be selected from the group consisting of: $^{11}$C-methoxy, $^{18}$F-fluoromethoxy-, $^{18}$F-fluoroethoxy-, and $^{18}$F-fluoropropoxy-, and methods of generating the probe.

In some embodiments of this aspect of the disclosure, the pharmaceutically acceptable probe composition can comprise a probe having the formula:

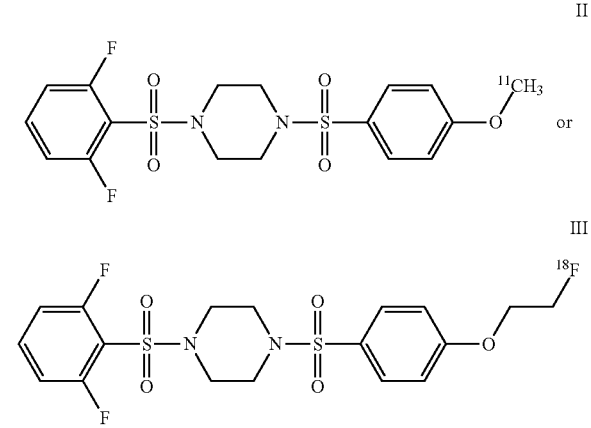

The disclosure further provides embodiments of a method of detecting a cell or a population of cells expressing pyruvate kinase M2, said method comprising: (i) contacting a cell or population of cells with a pharmaceutically acceptable PET-detectable radiolabelled probe composition comprising at least one probe having a radionuclide and having the formula:

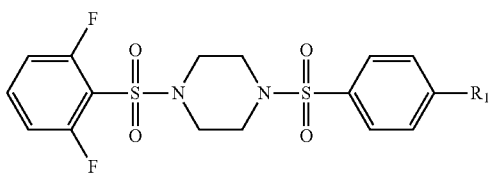

wherein $R_1$ can be selected from the group consisting of: $^{11}$C-methoxy, $^{18}$F-fluoromethoxy-, $^{18}$F-fluoroethoxy-, and $^{18}$F-fluoropropoxy; and (ii) detecting pyruvate kinase M2-specific binding of the radionuclide-containing probe within the cell or population of cells by detecting the presence of the radionuclide in the cell or population of cells. In some embodiments of this aspect of the disclosure detection of the radionuclide can be by Positron Emission Tomography (PET).

The probes and the methods of use thereof are advantageous for the detection and imaging of tumors, and are especially useful for the detection and imaging of tumors such as gliomas of the brain since the probes are able to traverse the blood-brain barrier.

BRIEF DESCRIPTION OF THE DRAWINGS

Aspects of the present disclosure will be more readily appreciated upon review of the detailed description of its various embodiments, described below, when taken in conjunction with the accompanying drawings. The drawings are described in greater detail in the description and examples below.

FIG. 1A illustrates that pyruvate kinase catalyzes the final step of glycolysis, resulting in net ATP synthesis through the dephosphorylation of phosphoenolpyruvate. The pyruvate kinase M2 (PKM2) isozyme predominates in proliferating non-malignant and in tumor cells. Two quaternary PKM2 conformations exist as homo-dimeric or -tetrameric forms. Dimeric PKM2 has reduced affinity for phosphoenolpyruvate in comparison to the tetramer, with tumor PKM2 mainly present in the dimeric form, resulting in a buildup of glycolytic precursors for use in biosynthetic processes. Conversely, PKM2 is mostly present in the tetrameric form in non-malignant cells.

FIG. 1B illustrates that PKM2 conformation is governed by intracellular concentrations of fructose-1,6-bisphosphate, direct oncogene regulation, and pharmacologically through PKM2 activators.

FIG. 2A illustrates a scheme for the synthesis of precursor 4-((4-((2,6-difluorophenyl)sulfonyl)piperazin-1-yl)sulfonyl)phenol and the radiolabeling of the $^{11}$C-labeled compound [$^{11}$C]DASA-23 (1-((2,6-difluorophenyl)sulfon-yl)-4-((4-(methoxy-$^{11}$C)phenyl)sulfonyl)piperazine). The precursor for $^{11}$C-labelling was synthesized from [$^{12}$C]DASA-23 followed by [$^{11}$C]methylation. Reagents and conditions: (i) dichloromethane, triethylamine, 0° C., 1 h; (ii) dichloromethane, trifluoroacetic acid, 0° C., 1 h; (iii) dichloromethane, triethylamine, 0° C., 1 h; (iv) acetonitrile, [$^{11}$C]methyl triflate, NaOH, 80° C., 3 min.

FIG. 2B illustrates cell uptake and washout of [$^{11}$C]DASA-23 by human HeLa cervical adenocarcinoma cells. Data is mean±SD (n=3).

FIG. 2C illustrates cell uptake and washout of [$^{11}$C]DASA-23 by human U87 glioma cells.

Data is mean±SD (n=3).

Figure 3A:
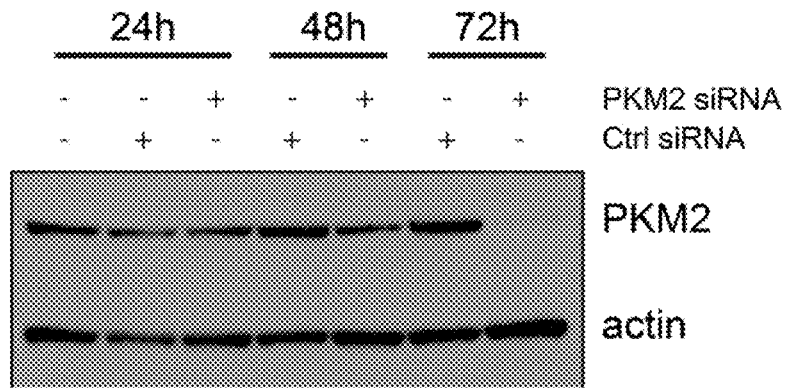
Figure 3B:
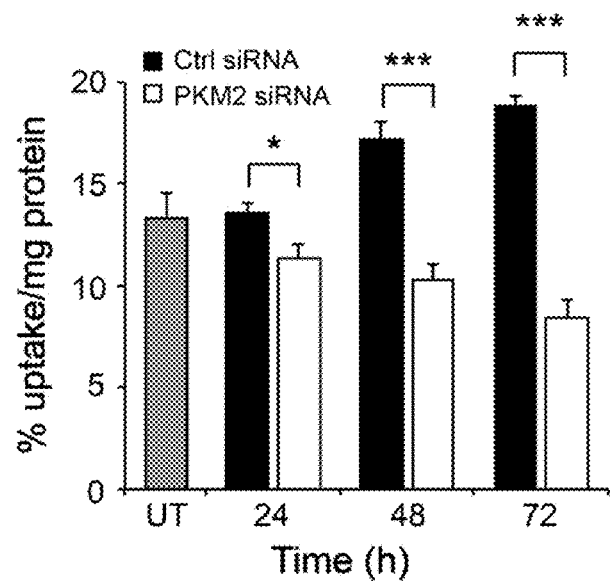
Figure 3C:
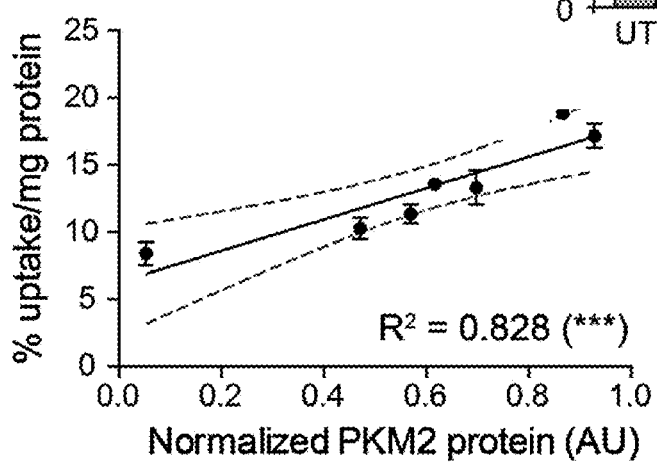

FIGS. 3A-3C illustrates the specificity for [$^{11}$C]DASA-23 to detect PKM2 expression in cells.

FIG. 3A illustrates a time-course of PKM2 knockdown by siRNA in HeLa cells in comparison to scrambled siRNA and untreated control cells. Representative western blot from whole cell lysate is shown, with actin used as a loading control.

FIG. 3B illustrates the associated [$^{11}$C]DASA-23 cell uptake following perturbation of PKM2 expression.

FIG. 3C illustrates the correlation between PKM2 protein expression and [$^{11}$C]DASA-23 uptake after PKM2 knockdown. 95% confidence levels are represented as dashed lines. Data shown as mean±SD (n=3). *, P=0.011; ***, P=0.0006, P=0.0001, and P=0.0045 for 24 h, 48 h, and 72 h siRNA treatment, and for the correlation between PKM2 protein and [$^{11}$C]DASA-23 uptake, respectively. Abbreviations: UT, untreated; Ctrl, control.

FIGS. 4A-4C illustrates PET/CT imaging, ex vivo biodistribution, and stability of [$^{11}$C]DASA-23 in mice bearing U87 glioblastoma xenografts.

FIG. 4A illustrates representative 30-60 min sagittal and axial fused PET/CT images. Nude mice received approximately 18.5 MBq of [$^{11}$C]DASA-23 via tail vein injection, with PET/CT images acquired 30-60 min post injection. Arrowheads indicate the tumor, identified from the CT image. Abbreviations: L, liver; S, salivary gland; SI, small intestine; K, kidney; B, bladder.

FIG. 4B illustrates the ex vivo biodistribution at 60 min p.i. Tumor-to-background ratios are shown. Data is mean±SD (n=6 animals). *, P<0.05; ***, P<0.001.

FIG. 4C illustrates the ex vivo mouse serum stability of [$^{11}$C]DASA-23. [$^{11}$C]DASA-23 was incubated in mouse serum for the allotted time points at 37° C. and compared to a [$^{11}$C]DASA-23 standard. Peak 1, [$^{11}$C]DASA-23; Peak 2, unknown metabolite.

FIGS. 5A-5C illustrates dynamic [$^{11}$C]DASA-23-PET image analysis of U87 tumor-bearing mice.

FIG. 5A illustrates temporal urinary excretion of [$^{11}$C]DASA-23.

FIG. 5B illustrates temporal hepatobiliary excretion of [$^{11}$C]DASA-23.

FIG. 5C illustrates tumor TAC representing average counts from a dynamic 60-min scan for U87 subcutaneous tumors compared to [$^{11}$C]DASA-23 uptake profiles for the muscle and normal brain. Data is mean±SD (n=3 animals).

FIGS. 6A-6D illustrate non-invasive imaging of mice bearing orthotopic U87 human gliomas.

Figure 6A:
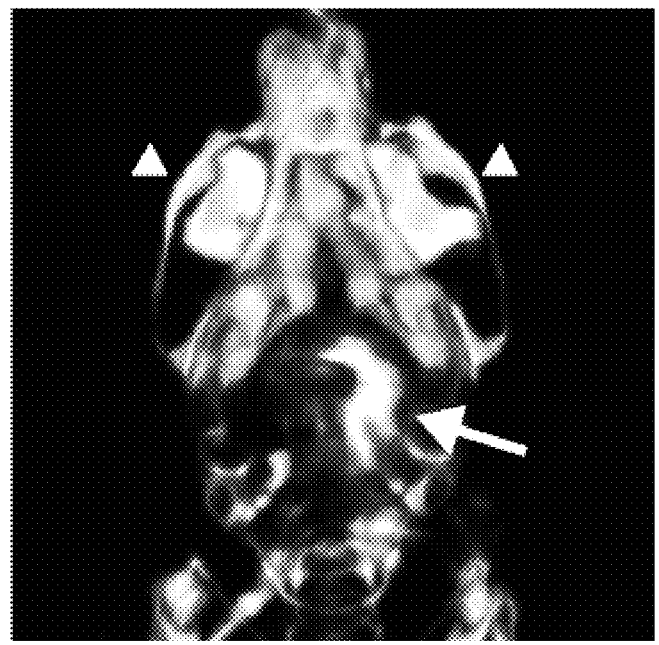

FIG. 6A illustrates a representative fused [$^{11}$C]DASA-23-PET/CT (10-30 min summed activity) 3D volume rendering technique (VRT) image of the head of a mouse containing an orthotopically-grown U87 tumor. The arrow indicates the tumor. [$^{11}$C]DASA-23 accumulation in the harderian glands is indicated by arrow heads.

Figure 6B:
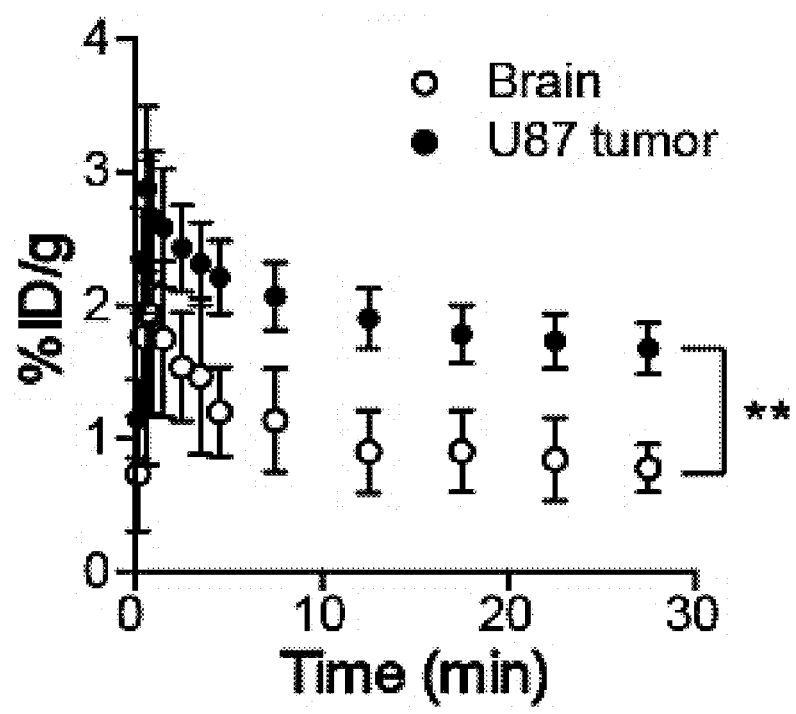

FIG. 6B illustrates orthotopic U87 tumor and corresponding contralateral normal brain TAC taken from dynamic [$^{11}$C]DASA-23-PET/CT images. Data is mean±SD (n=6 animals).

Figures 6C, 6D:
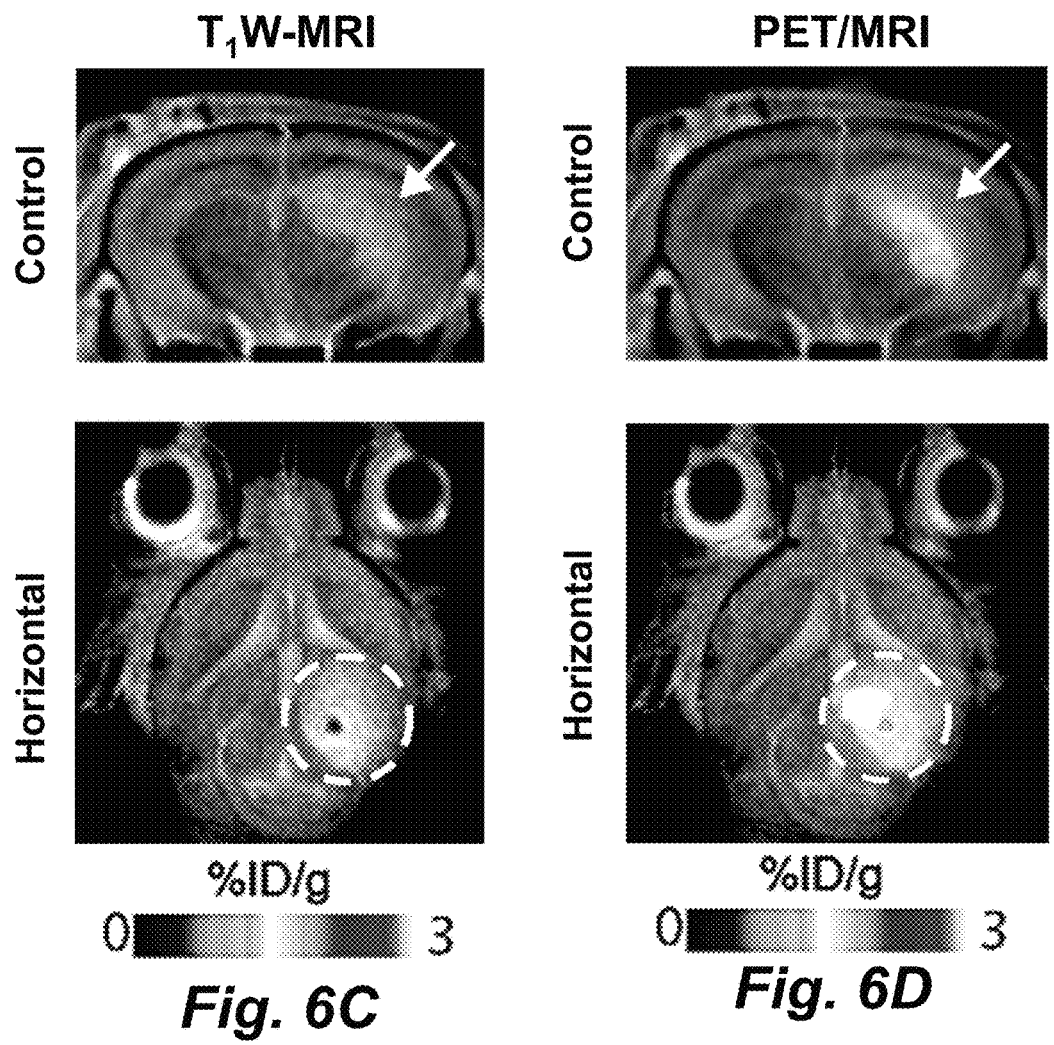

FIG. 6C illustrates representative contrast-enhanced $T_1$-weighted coronal and horizontal images of orthotopically-implanted U87 gliomas. $T_1$W-MRI, $T_1$-weighted nuclear magnetic resonance imaging.

FIG. 6D illustrates corresponding merged [$^{11}$C]DASA-23-PET/MR images (10-30 min summed [$^{11}$C]DASA-23 activity). Arrows and dashed circles indicate regions of contrast enhancement and radiotracer uptake, corresponding to the tumor.

Figure 7A:
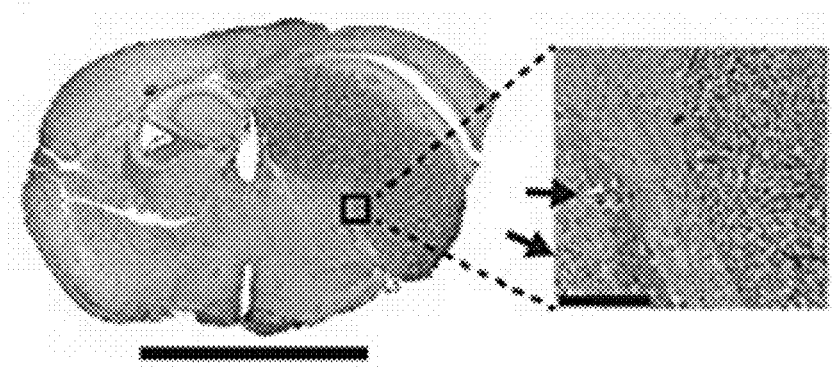
Figure 7B:
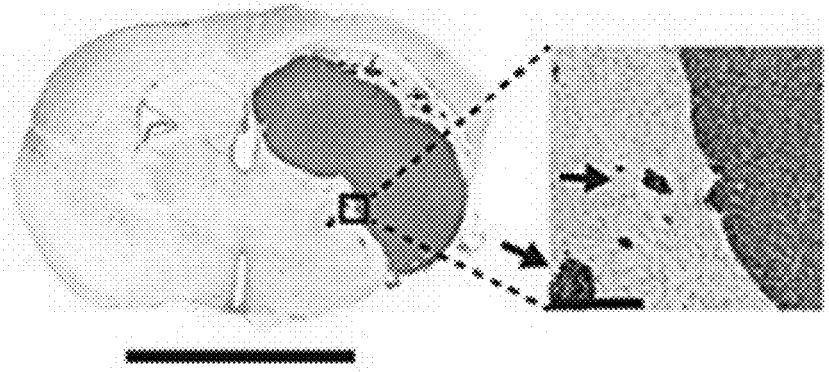
Figure 7C:
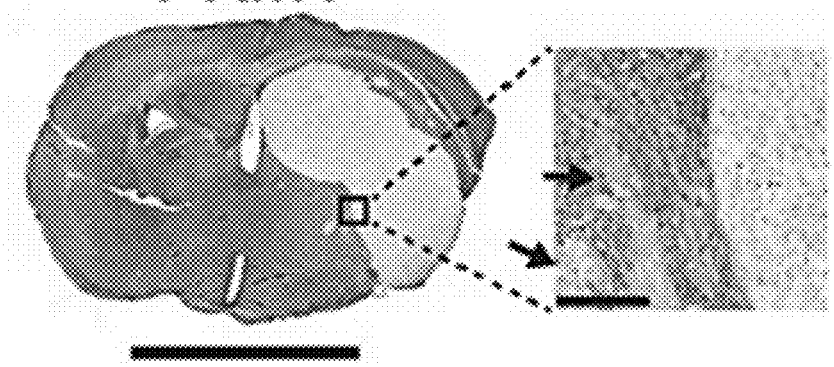

FIGS. 7A-7C illustrates a histopathological analysis of orthotopic U87 human gliomas.

FIG. 7A illustrates whole brain section stained with H&E (scale bar=5 mm). A higher magnification view of the area boxed in the tumor periphery is shown in the right-hand panel: 0.5×; scale bar=250 µm). Arrows indicate infiltrating U87 tumor cells away from the margins of the primary tumor.

FIG. 7B illustrates PKM2 immunohistochemistry staining of adjacent whole brain section (scale bar=5 mm). A higher magnification views of the area boxed is shown in the right-hand panel (10×; scale bar=250 µm).

FIG. 7C illustrates PKM1 immunohistochemistry staining of adjacent whole brain section (scale bar=5 mm. A higher magnification views of the area boxed is shown in the right-hand panel (10×; scale bar=250 µm).

FIGS. 8A-8E illustrates an assessment of TEPP-46 binding efficacy with [$^{11}$C]DASA-23 in orthotopic GBM39 PDX tumors.

FIG. 8A illustrates bioluminescence imaging of an orthotopically-implanted GBM39 tumor 50 days after injection.

FIG. 8B illustrates [$^{11}$C]DASA-23 PET/CT (10-30 min summed activity) images of the head of a GBM39 tumor-bearing mouse at baseline, reimaged the following day 1 hour after TEPP-46 injection (50 mg/kg i.p.). Arrows indicate the location of the tumor.

FIG. 8C illustrates 3D VRT (volume rendering technique) images of the same animal. Arrows indicate the location of the tumor. H, harderian glands; S, salivary glands.

Figure 8D:
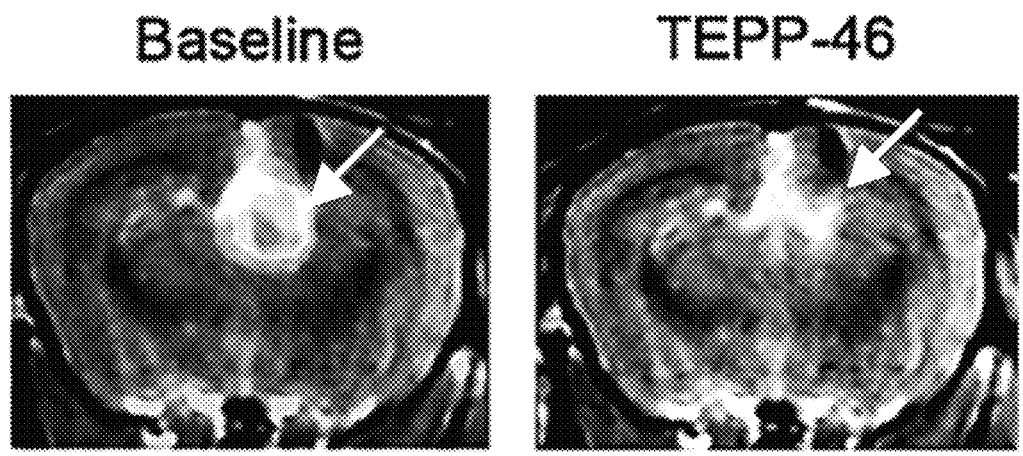

FIG. 8D illustrates merged [$^{11}$C]DASA-23-PET/MR images (10-30 min summed [$^{11}$C]DASA-23 activity) at baseline and after TEPP-46 injection. Arrows indicate the location of the tumor.

Figure 8E:
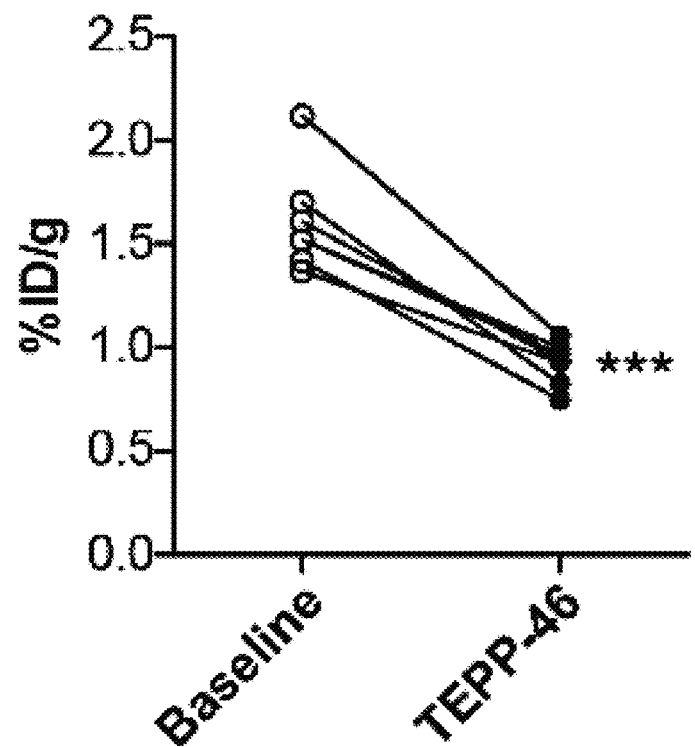

FIG. 8E illustrates semi-quantitative uptake values in GBM39 tumors before and after TEPP-46 blocking, taken 30 min after [$^{11}$C]DASA-23 injection. Data shown as mean±SD (n=7 animals). VRT, volume rendering technique. ***, P<0.001.

Figure 9:
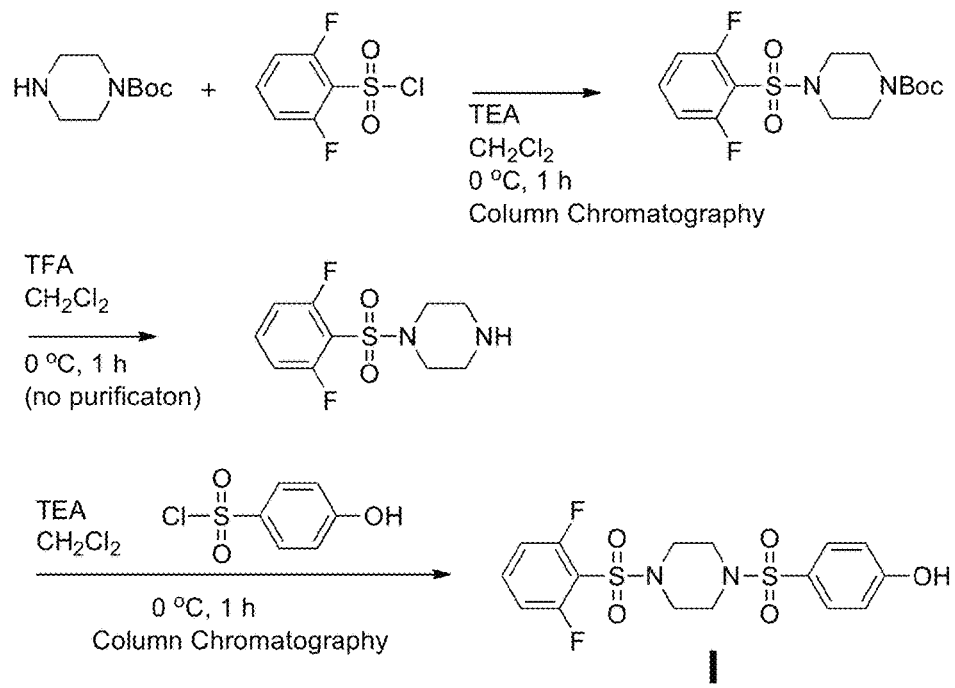

FIG. 9 illustrates Scheme A for the generation of the precursor 4-((4-((2,6-difluorophenyl)sulfonyl)piperazin-1-yl)sulfonyl)phenol (I).

Figure 10:
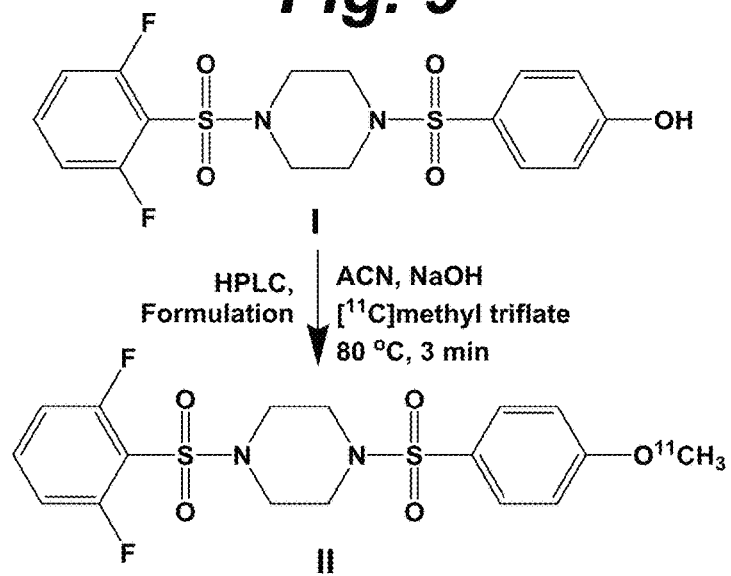

FIG. 10 illustrates Scheme B for the generation of the radiolabelled pyruvate kinase M2-specific probe II.

Figure 11:
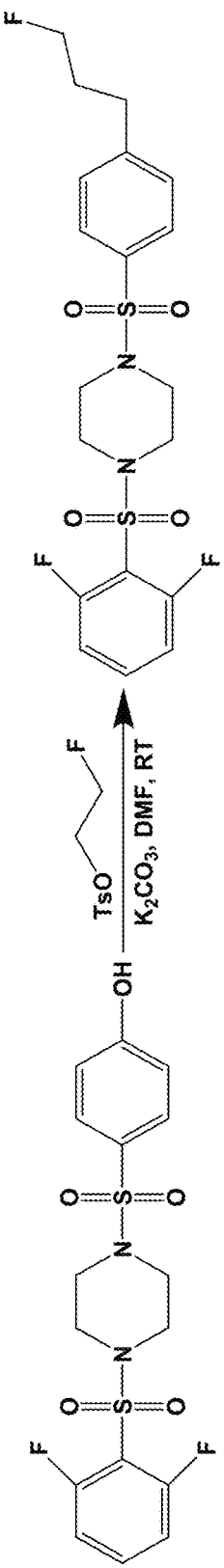

FIG. 11 illustrates scheme for the generation of unlabelled pyruvate kinase M2-specific probe.

Figure 12:
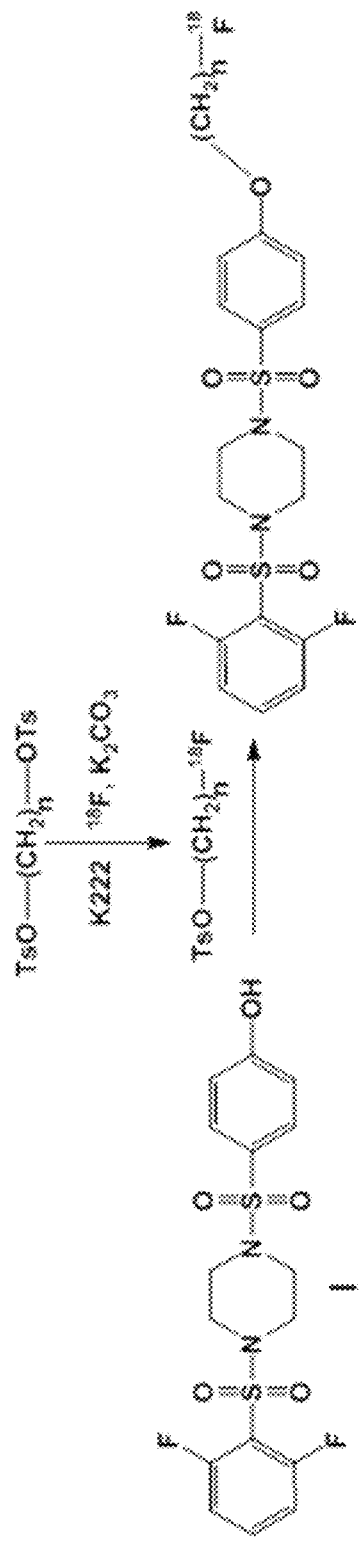

FIG. 12 illustrates the generalized Scheme C for the generation of the $^{18}$F-radiolabelled pyruvate kinase M2-specific probe derivatives.

Figure 13:
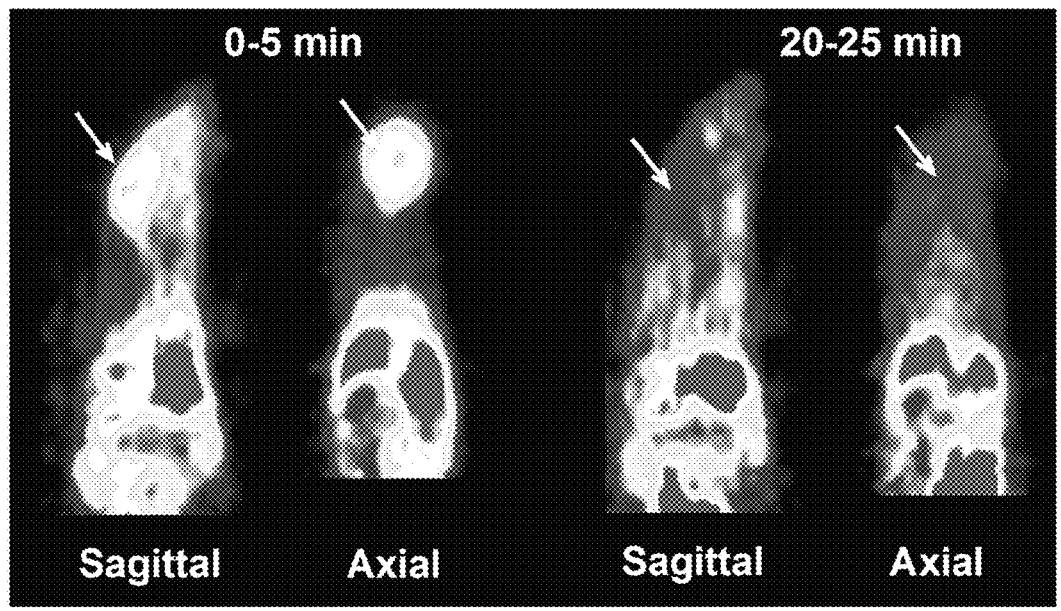

FIG. 13 illustrates [$^{18}$F]FE-PKM2 PET/CT images (2 h post-injection) in non-tumor-bearing mice. Arrows indicate the brain. There is evidence that this tracer crosses the blood brain barrier efficiently, and there is no observable defluorination, which is a typical problem with $^{18}$F-labeled PET tracers.

Figure 14:
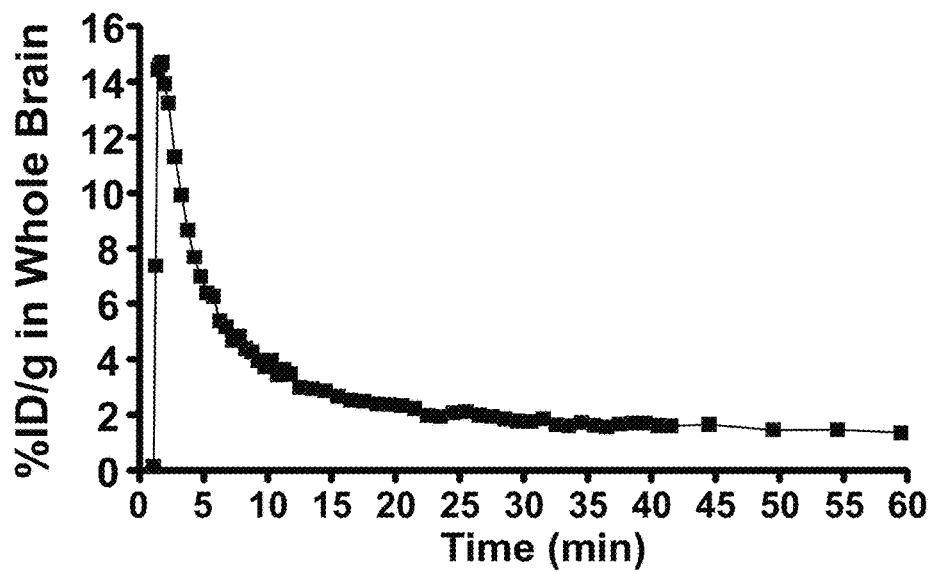

FIG. 14 illustrates [$^{18}$F]FE-PKM2 dynamic PET in the normal brain.

Figure 15:
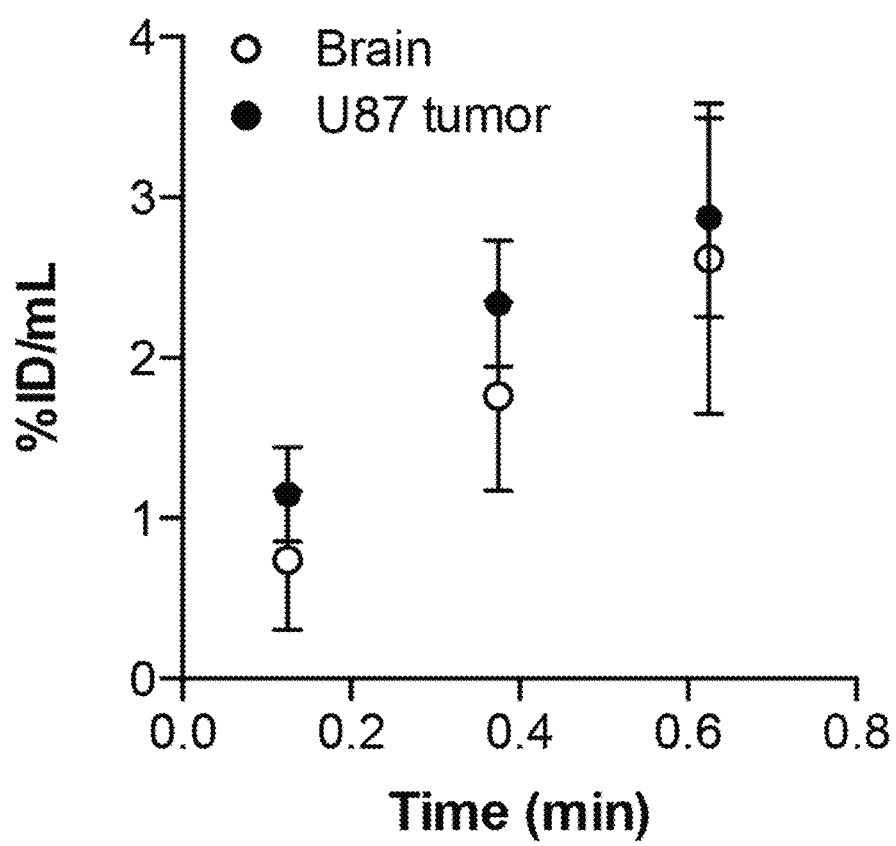

FIG. 15 illustrates the initial delivery of [$^{11}$C]DASA-23 to orthotopic U87 tumors and corresponding contralateral normal brain. The TAC was taken from dynamic [$^{11}$C]DASA-23-PET/CT images. Data shown as mean±SD (n=6 animals).

Figure 16:
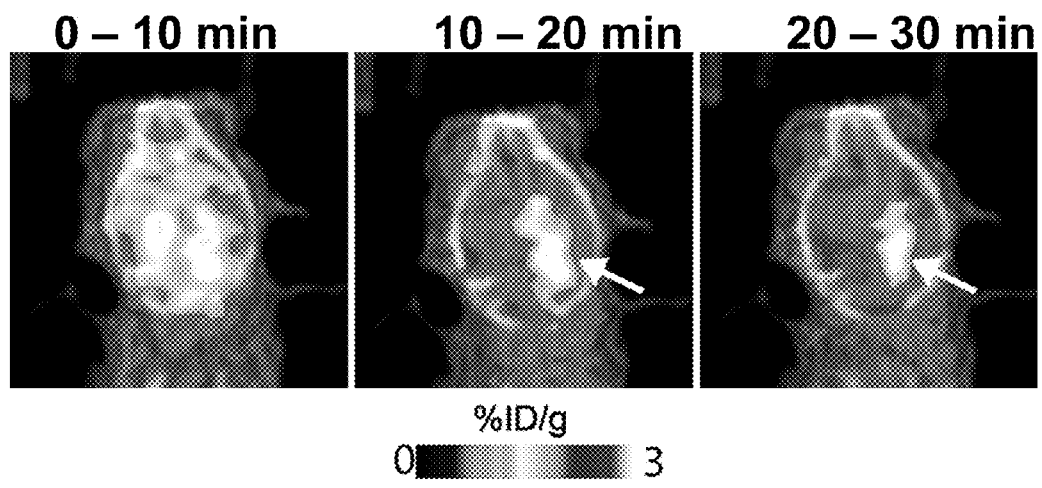

FIG. 16 illustrates time course images of [$^{11}$C]DASA-23 uptake in the brain of an orthotopic U87 tumor-bearing mouse. [$^{11}$C]DASA-23 PET/CT was characterized by rapid uptake and subsequent efflux in healthy brain tissue, with radioactivity retained in the tumor, as identified by the white arrows.

Figure 17:
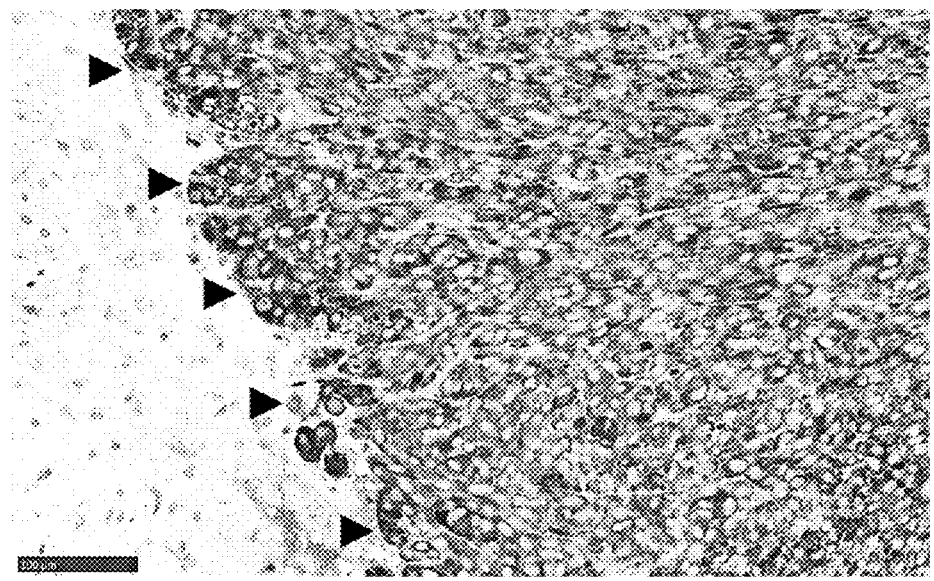

FIG. 17 illustrates cytosolic immunostaining of tumor-specific PKM2 at the tumor margin. PKM2 staining is denoted by black arrow heads (20×; scale bar=100 µm).

Figure 18:
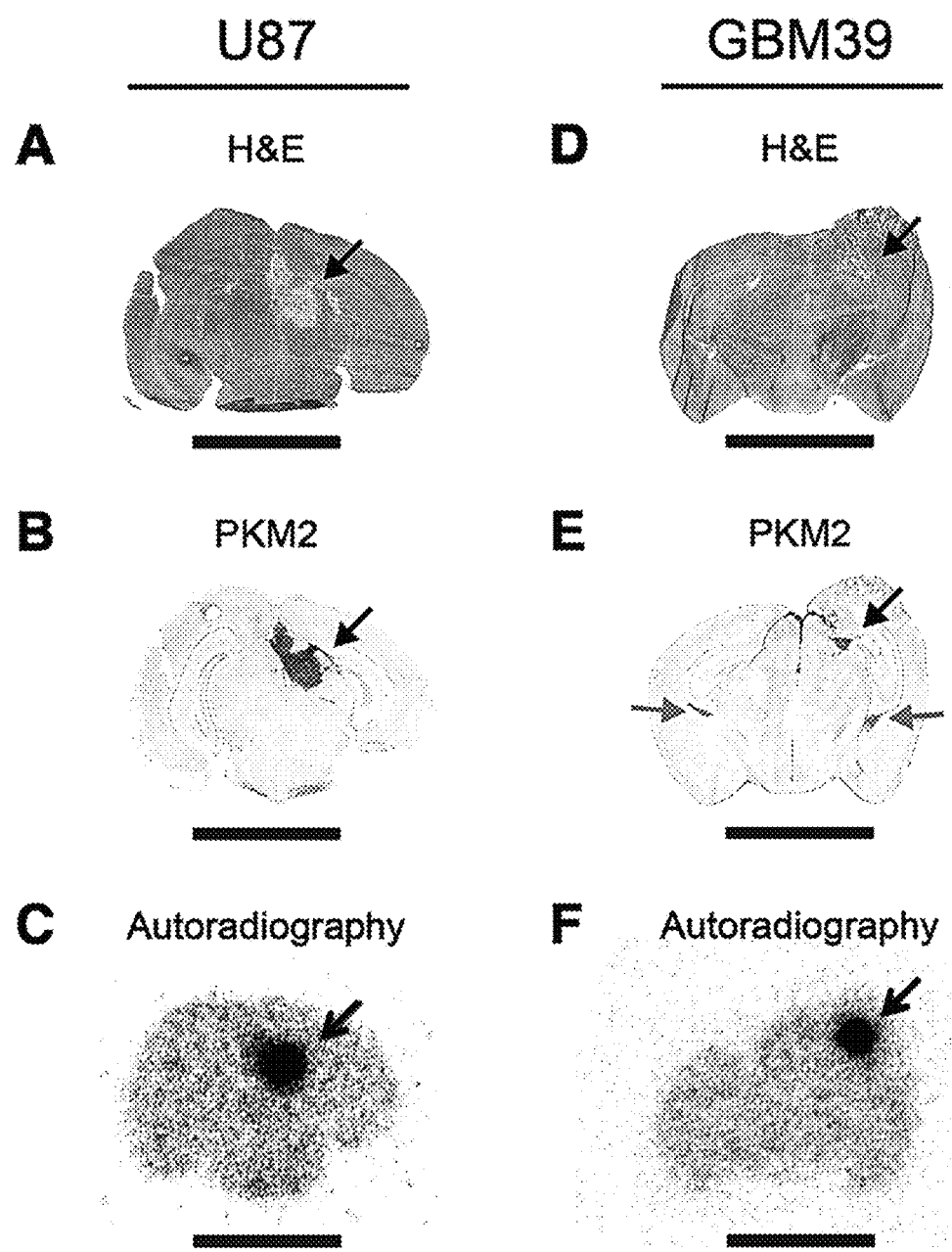

FIG. 18 illustrates ex vivo histopathological and autoradiographic analysis of orthotopic GBM tumors. [$^{11}$C]DASA-23 uptake and correlation with tumor-associated PKM2 expression was assessed in U87 (Panels A-C) and GBM39 tumors (Panels D-F). Whole brain sections were stained with either hematoxylin/eosin (H&E) (Panels A and D) or an antibody against PKM2 (Panels B and E), and compared to adjacent [$^{11}$C]DASA-23 ex vivo autoradiography sections taken 20 min after radiotracer injection (Panels C and F). Scale bar=5 mm. Arrows identify the tumor. Lowest arrows (Panel D) indicate PKM2 staining of suspected small tumor lesions not present in adjacent sections, as shown by H&E.

DESCRIPTION OF THE DISCLOSURE

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the"

include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean " includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law, allowing for the presence of more than that which is recited so long as basic or novel characteristics of that which is recited is not changed by the presence of more than that which is recited, but excludes prior art embodiments.

Definitions

In describing and claiming the disclosed subject matter, the following terminology will be used in accordance with the definitions set forth below.

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

The term "cancer," as used herein shall be given its ordinary meaning and is a general term for diseases in which abnormal cells divide without control. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue, such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it with differing processes that have gone awry. Solid tumors may be benign (not cancerous) or malignant (cancerous). Different types of solid tumors are named for the type of cells that form them. Examples of solid tumors are sarcomas, carcinomas, and lymphomas. Leukemias (cancers of the blood) generally do not form solid tumors. Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, and cervical cancer.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult.

Benign tumors have less of a tendency to invade and are less likely to metastasize. Brain tumors spread extensively within the brain but do not usually metastasize outside the brain.

Gliomas are very invasive inside the brain, even crossing hemispheres. They divide in an uncontrolled manner and, depending on their location, they can be as life threatening as other types of malignant lesions. For example, a glioma can grow and occupy space within the skull, leading to increased pressure on the brain.

The term "activator" as used herein refers to stimulating, enhancing, increasing, or upregulating pyruvate kinase activity, as measured by any method, technique, signal, detector or indicator that is known in the art to be indicative of pyruvate kinase activity.

The term "cell or population of cells" as used herein refers to an isolated cell or plurality of cells excised from a tissue or grown in vitro by tissue culture techniques. In the alternative, a population of cells may also be a plurality of cells in vivo in a tissue of an animal or human host.

The term "contacting a cell or population of cells" as used herein refers to delivering a composition such as, for example, a probe composition according to the present disclosure with or without a pharmaceutically or physiologically acceptable carrier to an isolated or cultured cell or population of cells, or administering the probe in a suitable pharmaceutically acceptable carrier to an animal or human host. Thereupon, it may be systemically delivered to the target and other tissues of the host, or delivered to a localized target area of the host. Administration may be, but is not limited to, intravenous delivery, intraperitoneal delivery, intramuscularly, subcutaneously or by any other method known in the art. One method is to deliver the composition directly into a blood vessel leading immediately into a target organ or tissue such as a prostate, thereby reducing dilution of the probe in the general circulatory system. It is contemplated that in the methods of the disclosure, administration or delivering a probe to an animal or human subject will result in the probe contacting a cell or population of cells (most advantageously a cancer cell or population of cancer cells). The probe may then enter the cell by active or passive transport.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probes of the disclosure and pharmaceutically acceptable carriers preferably should be sterile. Water is a useful carrier when the probe of the disclosure is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "positron emission tomography" as used herein refers to a nuclear medicine imaging technique that produces a three-dimensional image or map of functional processes in the body. The system detects pairs of gamma rays emitted indirectly by a positron-emitting radioisotope, which is introduced into the body on a metabolically active molecule. Images of metabolic activity in space are then reconstructed by computer analysis. Using statistics collected from tens-of-thousands of coincidence events, a set of simultaneous equations for the total activity of each parcel of tissue can be solved by a number of techniques, and a map of radioactivities as a function of location for parcels or bits of tissue may be constructed and plotted. The resulting map shows the tissues in which the molecular probe has become concentrated. Radioisotopes used in PET scanning are typically isotopes with short half-lives such as carbon-11 ($^{11}$C) (about 20 min), nitrogen-13 ($^{13}$N) (about 10 min), oxygen-15 ($^{15}$O) (about 2 min), and fluorine-18 ($^{18}$F) (about 110 min). PET technology can be used to trace the biologic pathway of any compound in living humans (and many other species as well), provided it can be radiolabeled with a PET isotope. The half-life of fluorine-18 (18F) is long enough such that fluorine-18 labeled radiotracers can be manufactured commercially at an offsite location.

The term "label" as used herein refers to any moiety that may be linked (e.g. bonded or otherwise associated with) to the compounds of the present disclosure and which may be used to provide a detectable image including PET agents such as, but not limited to, $^{11}$C, $^{18}$F, $^{124}$I, and $^{64}$Cu; or SPECT agents such as, $^{123}$I, $^{125}$I, or $^{131}$I.

The term "in vivo imaging" as used herein refers to methods or processes in which the structural, functional, or physiological state of a living being is examinable without the need for a life-ending sacrifice.

The term "non-invasive in vivo imaging" as used herein refers to methods or processes in which the structural, functional, molecular, or physiological state of being is examinable by remote physical probing without the need for breaching the physical integrity of the outer (skin) or inner (accessible orifices) surfaces of the body.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

Abbreviations

PET, Positron Emission Tomography; MRI, Magnetic Resonance Imaging; PK, pyruvate kinase; PKM2 splice variant of pyruvate kinase; PEP, phosphoenylpyruvate; DASA, N,N-diarylsulfonamide; TEPP-46, 6-((3-Aminophenyl)methyl)-4-methyl-2-methylsulfinylthieno[3,4]pyrrolo[1,3-d]pyridazin-5-one; i.p.: intraperitoneal; s.c.: subcutaneous; i.v.: intravenous.

Discussion

Figure 1A:
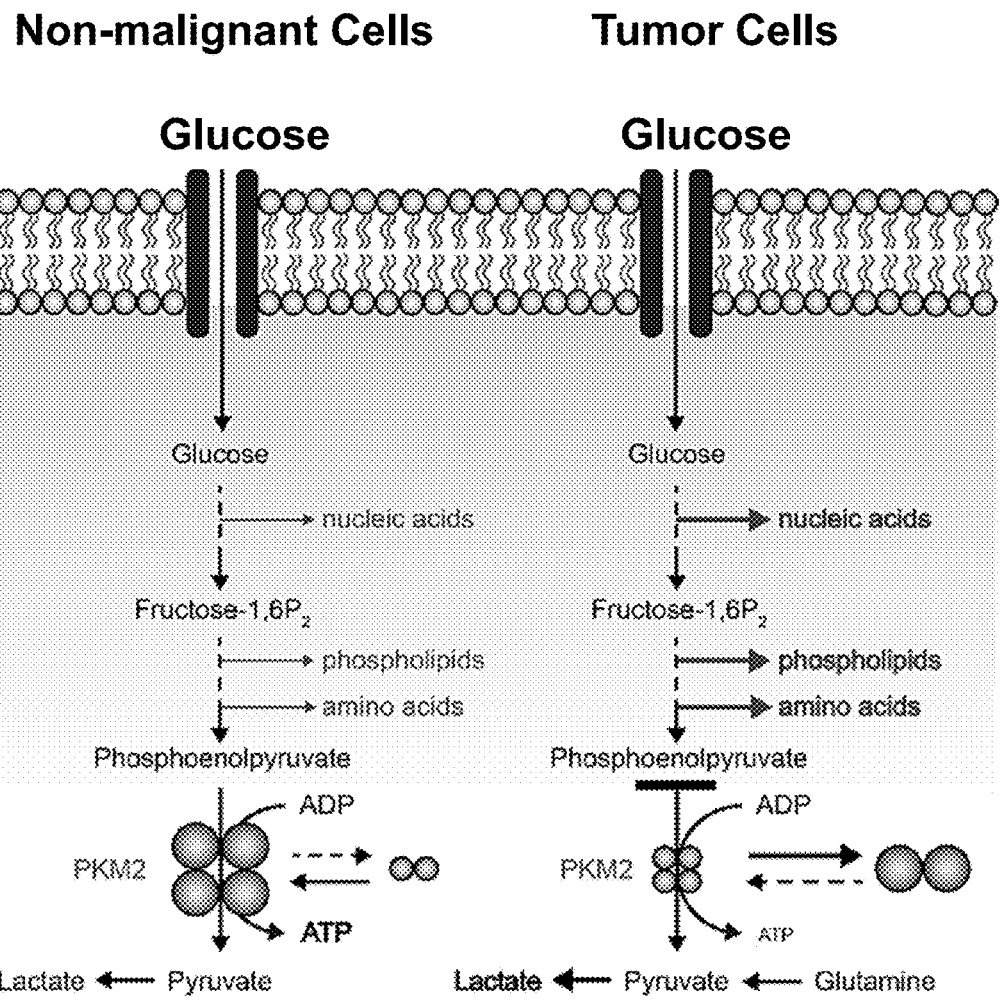
FIGS. 1A and 1B schematically illustrate the control of non-malignant and tumor glycolysis by pyruvate kinase M2 (PKM2).
Figure 1B:
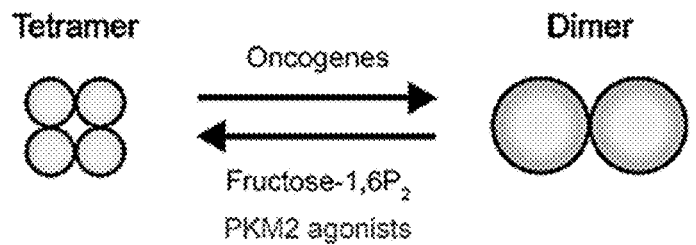

Pyruvate Kinase: Pyruvate kinase (PK) catalyzes the final and rate-limiting reaction in glycolysis, converting phosphoenolpyruvate (PEP) to pyruvate by transferring the high-energy phosphate group to ADP to produce ATP. PK consists of four isoforms, of which the spliced variant, PKM2, is preferentially expressed in all cancers studied to-date, regardless of their tissue of origin (Wong et al., (2013) Int. J. Cell Biol. 2013: 242513). PKM2 is allosterically regulated by the stabilization of a highly active tetramer relative to monomeric/dimeric PKM2. The tetramer of PKM2 has a high affinity for PEP, favoring synthesis of ATP and pyruvate, whereas the monomer/dimer has reduced activity because of its low affinity for PEP at physiological concentrations (Dombrauckas et al., (2005) Biochemistry 44: 9417-9429). When PKM2 is in the monomeric/dimeric conformation, reduced glycolytic flux through to pyruvate results in the accumulation of precursors for the biosynthesis of amino acids, nucleic acids, and phospholipids, commensurate with the production of reducing power through pentose phosphate pathway-derived NADPH (Mazurek S. (2011) Int. J. Biochem. Cell Biol. 43: 969-980). A dynamic equilibrium between the two states of PKM2 enables tumor cells to switch between anabolic and catabolic metabolism, as shown in FIG. 1A. Alternative splicing of PKM2 is controlled by c-Myc and HIF-1 oncogenes (Chaneton & Gottlieb (2012) Trends Biochem. Sci. 37: 309-316), with quaternary structure of PKM2 tightly regulated by the glycolytic intermediate fructose 1,6-bisphosphate (FBP) (Bailey et al., (1968) Biochem J. 108: 427-436) and growth factor signaling (Christofk et al., (2008) Nature 452: 181-186), as shown in FIG. 1B. In recent years, PKM2 has been targeted for cancer therapy through the development of small molecule activators that promote tetramer formation (Boxer et al., (2010) J. Med. Chem. 53: 1048-1055; Israelsen et al., (2013) Cell 155: 397-409).

Tumor cells reprogram their metabolism in response to the increased anabolic and catabolic demands of highly-proliferative cells. For many metabolic pathways, the balance between biomolecular synthesis and energy production is highly regulated. An elegant example is provided in the case of acetyl CoA carboxylase, which controls the opposing rates of fatty acid synthesis and oxidation on the basis of intracellular concentrations of acetyl CoA and malonyl CoA (Tong L. (2005) Cell. Mol. Life Sci. 62: 1784-1803). Altered tumor glycolysis is mediated, in part, by PKM2 through transcriptional and epigenetic means (David et al., (2010) Nature 463: 364-U114; Luo et al. (2011) Cell 145: 732-744;

Lv et al. (2011) *Mol. Cell* 42: 719-730), with a growing body of evidence demonstrating a critical role of PKM2 in tumorigenesis and progression (Wong et al., (2013) *Int. J. Cell Biol.* 2013: 242513). Further evidence suggests that PKM2 might provide a similar regulatory switch to acetyl CoA carboxylase; controlling the balance between glycolytically-derived anabolic and catabolic metabolism (Mazurek S. (2011) *Int. J. Biochem. Cell Biol.* 43: 969-980; Christofk et al., (2008) *Nature* 452: 181-186; Eigenbrodt et al., (1992) *Critical Revs Oncogenesis* 3: 91-115; Vander Heiden et al., (2009) *Science* 324: 1029-1033). PKM2 has additionally been shown to translocate to the nucleus where it functions to promote cell proliferation through interaction with HIF, STAT 3, Oct 4 and β-catenin (reviewed in Chaneton & Gottlieb (2012) *Trends Biochem. Sci.* 37: 309-316)).

Although of great interest and importance, non-invasive imaging of PKM2 with clinically-relevant probes and imaging modalities has not yet been reported. PKM2 is overexpressed in tumors (Wong et al., (2013) *Int. J. Cell Biol.* 2013: 242513) and expressed in most tissues to varying degrees, with the exception of adult muscle, brain and liver (Bluemlein et al. (2011) *Oncotarget* 2: 393-400; Christofk et al. (2008) *Nature* 452: 230-233; Imamura & Tanaka (1972) *J. Biochem.* 71: 1043-1051).

Figure 2A:
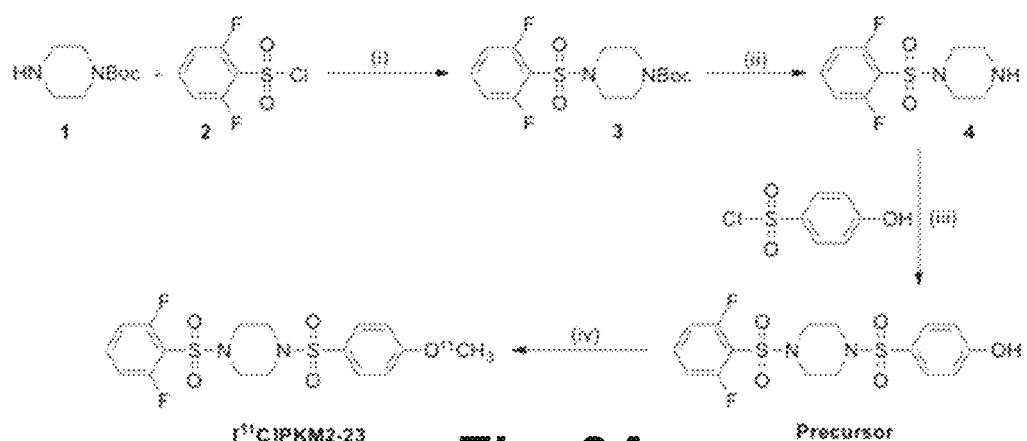
FIGS. 2A-2C illustrate radiosynthesis, tumor cell uptake, retention and washout of [$^{11}$C]DASA-23.

Given the importance of PKM2 in the regulation of tumor metabolism, there is an on-going need to noninvasively measure its expression through the development of PKM2-specifc radiopharmaceuticals. A class of N,N-diarylsulfonamides (DASA) was reported by Boxer et al. in 2010 as PKM2 activators (Boxer et al., (2010) *J. Med. Chem.* 53: 1048-1055), known to promote PKM2 tetramer formation through binding at the subunit interaction interface of the PKM2 dimer in an allosteric pocket that is distinct from the binding site of fructose 1,6-bisphosphate, thereby inhibiting tumor growth in vivo (Anastasiou et al., *Nat. Chem. Biol.* 8: 839-847). The synthesis and evaluation of a novel positron emission tomography (PET) radiotracer for dimeric PKM2, [$^{11}$C]DASA-23, based on this class of compounds as shown in FIG. 2A.

Accordingly, the ability of [$^{11}$C]DASA-23 to detect tumor-specific PKM2 in subcutaneous and orthotopic mouse models of human glioma in vivo is now demonstrated. The in vivo specificity and selectivity of [$^{11}$C]DASA-23 for PKM2 through pharmacological challenge in mice bearing patient-derived orthotopic xenografts (PDX) treated with TEPP-46, a structurally distinct class of PKM2 activator is now also shown.

The present disclosure, therefore, provides PET-detectable probes that can selectively bind to the pyruvate kinase variant M2 (PKM2) that is found in cancer cells. It is further contemplated that the probes of the disclosure can be advantageously used to detect PKM2 expression in cells other than just cancer cells. In the embodiments of the radiolabeled probes of the disclosure the radionuclide conjugated thereto can be, but is not limited to, the isotopes $^{11}$C or $^{18}$F. In some preferred embodiments the radionuclide is $^{11}$C. In other embodiments of the radiolabeled probes of the disclosure, the radioisotope, and most advantageously the $^{18}$F isotope is provided as $^{18}$F-fluoromethoxy-, $^{18}$F-fluoroethoxy-, or $^{18}$F-fluoropropoxy-.

The present disclosure encompasses novel synthetic procedures for radiolabeling the PKM2 activator DASA-23 by introducing the $^{11}$C label or the $^{18}$F label to the novel precursor 4-((4-((2,6-difluorophenyl)sulfonyl)piperazin-1-yl)sulfonyl)phenol(I), itself generated by a novel synthetic pathway (Scheme A, as shown in FIG. 9). Further, since the half-life of the $^{11}$C isotope is approximately 20.5 min, it is advantageous for a practitioner desirous of administering the probes of the disclosure to a patient for the purposes of generating a PET image thereof to attach the radionuclide to the precursor shortly before administration. It is contemplated, therefore, that a precursor compound suitable for receiving the radionuclide and capable of specifically binding to the PKM2 variant, may be provided. Methods, therefore, are provided for the generation of such a precursor and the radiolabeling of such. Most advantageously, a suitable precursor can have the formula (I) as shown in FIG. 9.

The present disclosure further demonstrates the advantage that the PKM2-specific radiolabeled probe can surprisingly traverse the blood-brain barrier and then allow imaging of cancer cells such as gliomal cells in the brain. Accordingly, the probes of the disclosure allow methods of acquiring images, and in particular PET images, of tumors in the brain, in the prostate, and in other tissues.

Figure 2B:
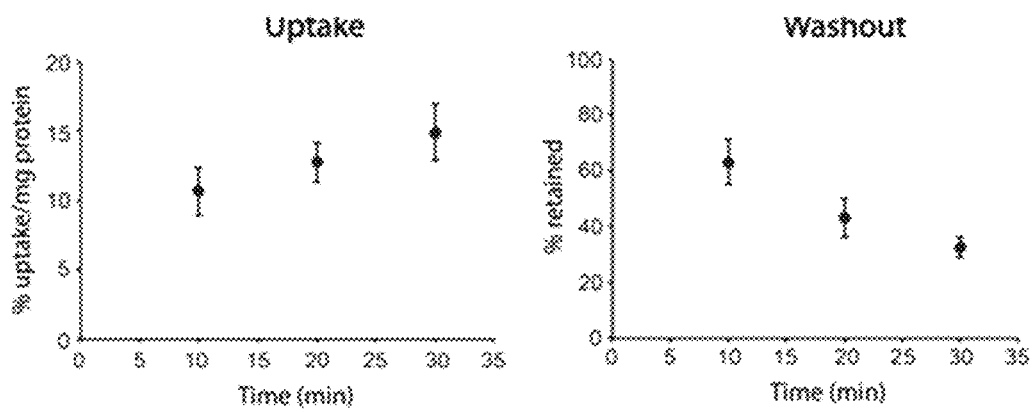
Figure 2C:
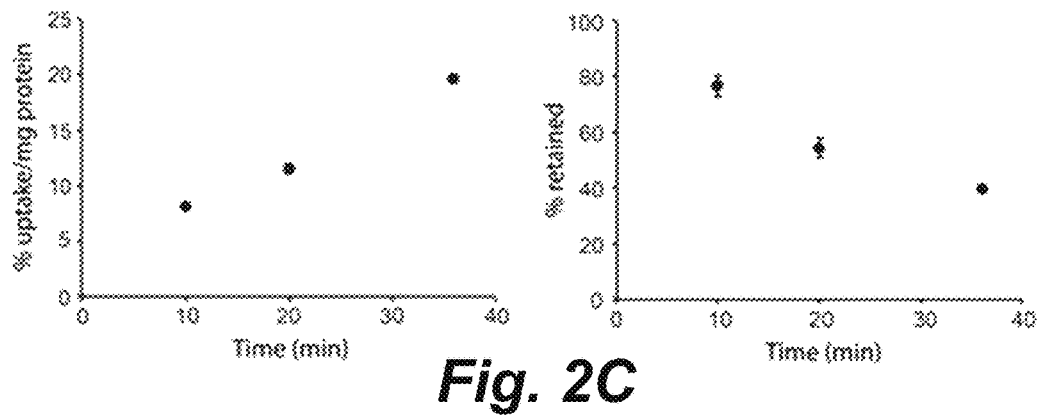

Given the intrinsically low background of PKM2 in the brain, it was considered whether PKM2 is up-regulated in transformed human glioblastoma cells, using orthotopic mouse models of the disease, and whether it was possible to measure this transformation non-invasively through imaging. By using the $^{11}$C-labelled PKM2 activator $^{11}$C-DASA-23 (II), which displays selective activation of PKM2 ($AC_{50}$=90 nM) versus other pyruvate kinase isozymes, PKM1, PKR and PKL (Boxer et al., (2010) *J. Med. Chem.* 53: 1048-1055), high tumor cell uptake of the tracer in culture is now demonstrated, with uptake strongly correlated to PKM2 protein expression (FIGS. 2C, 2D and FIGS. 3A-3C). As DASA-23 reversibly binds to PKM2, efflux of the tracer from tumor cells following removal of exogenous activity was expected, although this occurred at a relatively slow rate (FIGS. 2B and 2C). Of note was the ability of [$^{11}$C]DASA-23 to measure increased PKM2 expression following prolonged incubation in media (up to 72 h; FIG. 3B). Cell adaptation to a reduced nutrient environment, akin to poorly perfused tumors in vivo, hints at an important role for PKM2 in the maintenance of metabolic homeostasis. PKM2 is degraded when glucose is abundant via acetylation and chaperone-mediated autophagy, a process which is inhibited under nutrient stress (Lv et al. (2011) *Mol. Cell* 42: 719-730). The ability to detect these chronically nutrient-deprived cells, through PKM2 imaging, may provide novel insights into tumor progression and metastasis, given that these cells are relatively chemoresistant (Gatenby & Gillies (2004) *Nature Revs. Cancer* 4: 891-899).

Given the good in vitro uptake profile and relatively high lipophilicity (cLogP=3.4, ChemDraw Bio 13.0) of [$^{11}$C]DASA-23 (required for diffusion across the blood brain barrier), [$^{11}$C]DASA-23 was examined for suitability for use in pre-clinical in vivo imaging of a human glioma. [$^{11}$C]DASA-23 could clearly image subcutaneous U87 tumor xenografts. The combined renal and hepatobiliary excretion profile for [$^{11}$C]DASA-23, however, indicates that this probe is advantageous for the imaging of PKM2 to tumors of the brain after rapid initial uptake and washout, and of the upper thoracic region. Tumor-to-muscle and blood background ratios, although statistically significant, were below those typically observed with FDG-PET (Witney et al., (2015) *Clin. Cancer Res.* 21: 3896-3905).

High-quality PET/MR images of orthotopically-grown U87 gliomas were obtained, with radioactivity confined to the tumor. Low background radioactivity was detected in normal tissue of the brain, as predicted by the absence of PKM2 expression previously measured in this tissue (Imamura & Tanaka (1972) *J. Biochem.* 71: 1043-1051), and shown here by immunohistochemistry (FIG. 7B). Indeed, PKM2 expression was exclusively confined to the intracranial tumor that lacks PKM1. Autoradiographic analysis of tumor sections after saline perfusion, which removed unbound/intravascular radioactivity from the brain, further confirmed tumor-specific binding of [¹¹C]DASA-23.

In addition, [¹¹C]DASA-23 could clearly image subcutaneous U87 tumor xenografts. [¹¹C]DASA-23 was excreted through both the renal and hepatobiliary routes, which may limit the imaging of PKM2 to tumors of the upper thoracic, for example brain and breast. Voiding of bladder radioactivity can also be useful to enable good prostate tumor delineation, given the urinary excretion profile of [¹¹C] DASA-23. This may be of particular importance as alterations in PKM2 have been associated with prostate cancer progression, tumor aggressiveness and a high Gleason score (Wong et al., (2014) *Cancer Investigation* 32: 330-338).

The increased glucose utilization of tumors in comparison to normal tissue (the "Warburg effect"), has previously been exploited clinically to detect tumors and their response to treatment by [¹⁸F]2-fluoro-2-deoxy-D-glucose ([¹⁸F]FDG) PET. ¹⁸F-FDG-PET is approved for use for the diagnosis of the majority of cancers (Kelloff et al. (2005) *Clin. Cancer Res.* 11: 2785-2808), with particular utility for detecting metastases and nodal disease that appear normal on x-ray computed tomography scans (Sharma et al. (2004) *Radiological Soc. North Am.* 24: 419-434). Some tumors however are not [¹⁸F]FDG-avid, e.g., prostate adenocarcinoma (Takahashi et al., (2007) *Oncology* 72: 226-233), whereas a high background uptake by surrounding normal tissue can mask tumor uptake, for example, in the brain (Phelps & Mazziotta J C (1985) *Science* 228: 799-809).

Accordingly, [¹¹C]DASA-23 is useful for the noninvasive measurement of malignancies where FDG has failed. Several other radiotracers, such as 3,4-dihydroxy-6-[¹⁸F]fluorophenylalanine ([¹⁸F]F-FDOPA) (Karunanithi et al., (2013) *Eur. J. Nucl. Med. Mol. Imaging* 40: 1025-1035), O-(2-[¹⁸F] fluoroethyl)-L-tyrosine (FET) (Weber et al., (2000) *Eur. J. Nucl. Med.* 27: 542-549), 4-[¹⁸F]-(2S,4R)-fluoroglutamine (Venneti et al., (2015) *Sci. Transl. Med.* 7: 274ra217, and (4S)-4-(3-[¹⁸F]fluoropropyl)-L-glutamate ([¹⁸F]FSPG) Baek et al., (2012) *Clin. Cancer Res.* 18: 5427-5437) have shown great value for imaging tumors of the brain. In contrast, the present disclosure encompasses probes directed to non-invasive measurement of PKM2 status in these tumors. It has now been found that the probes of the disclosure, such as [¹¹C]DASA-23 and derivatives thereof, can report on the binding efficacy of these agents to PKM2 using orthotopically-implanted PDX models of GBM. In these longitudinal studies, infiltrative GBM39 tumors were delineated by PET, with tumor-specific retention of [¹¹C] DASA-23 abolished after pretreatment of the same animals with a bolus of TEPP-46, a structurally distinct class of PKM2 activators known to bind the same allosteric site as the DASA-class of activators (Anastasiou et al., (2012) *Nat. Chem. Biol.* 8: 839-847). These data provide evidence of the in vivo specificity of [¹¹C]DASA-23 for reporting on tumor-specific PKM2 expression and a potential role for both drug screening and the evaluation of precision medicine strategies. Furthermore, the observation that temozolomide-treated glioblastomas have reduced PKM2 expression (Park et al., (2014) *Cancer Res.* 74: 7115-7124) indicates that [¹¹C]DASA-23 may also provide a means to measure the efficacy of more traditional therapeutics.

Regarding diagnostic utility, therefore, [¹¹C]DASA-23 can be advantageously employed in the non-invasive measurement of malignancies where FDG fails. Given the great interest in targeting PKM2 for cancer therapy (Boxer et al., (2010) *J. Med. Chem.* 53: 1048-1055; Anastasiou et al. (2012) *Nature Chem. Biol.* 8: 839-847; Vander Heiden et al. (2010) *Biochem. Pharmacol.* 79: 1118-1124; Walsh et al. (2011) *Bioorganic Med. Chem. Letts.* 21: 6322-6327), [¹¹C] DASA-23 and the derivatives thereof as described in the present disclosure, may also provide a means to measure the therapeutic efficacy of these novel agents.

Accordingly, a PKM2-binding PET radiotracer family has been developed that enables the specific and sensitive preclinical detection of orthotopically-growing human glioblastoma. This study sets the foundation for the clinical translation of [¹¹C]DASA-23 for the imaging of primary and metastatic gliomas. [¹¹C]DASA-23 PET and derivatives thereof can be useful as a companion diagnostic and for the assessment of tumor aggressiveness. DASA-23 was labeled here with ¹¹C to preserve the compound's specificity and selectivity for PKM2 binding (Boxer et al., (2010) *J. Med. Chem.* 53: 1048-1055). It is further contemplated that ¹⁸F-fluorination of DASA-23 at the methoxy group may be advantageous for the clinical utility of this radiotracer by increasing the radioisotope half-life from 20.3 min (carbon-11) to 109.8 min (fluorine-18).

One aspect of the disclosure, therefore, encompasses embodiments of a precursor useful for the radiosynthesis of a radiolabeled pyruvate kinase M2 activator, wherein said precursor is 4-((4-((2,6-difluorophenyl)sulfonyl)piperazin-1-yl)sulfonyl)phenol(I) and has the formula:

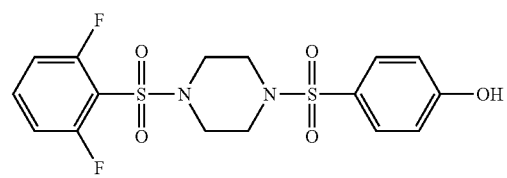

Another aspect of the disclosure encompasses embodiments of a method of generating a pyruvate kinase M2 activator precursor wherein said precursor is 4-((4-((2,6-difluorophenyl)sulfonyl)piperazin-1-yl)sulfonyl)phenol(I), wherein said method is according to scheme A, as shown in FIG. 9.

Yet another aspect of the disclosure encompasses embodiments of a pharmaceutically acceptable probe composition comprising a Positron Emission Tomography (PET)-detectable radiolabelled probe, wherein said probe has the formula:

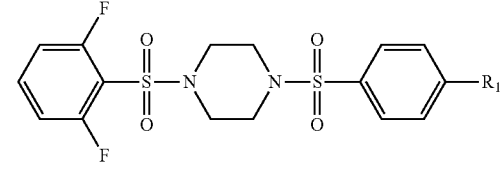

wherein $R_1$ can be selected from the group consisting of: ¹¹C-methoxy, ¹⁸F-fluoromethoxy-, ¹⁸F-fluoroethoxy-, and ¹⁸F-fluoropropoxy-.

In some embodiments of this aspect of the disclosure, the pharmaceutically acceptable probe composition can comprise a probe having the formula:

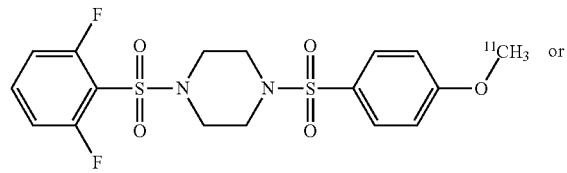

II

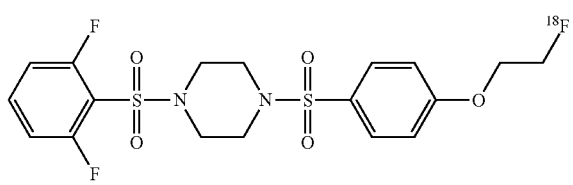

III

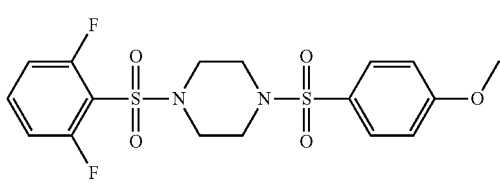

III

In some embodiments of this aspect of the disclosure, the pharmaceutically acceptable probe composition can further comprise a pharmaceutically acceptable carrier.

Yet another aspect of the disclosure encompasses embodiments of a method of generating a radiolabelled probe, wherein said method is according to scheme B, as shown in FIG. 10, or according to scheme C, as shown in FIG. 12.

Yet another aspect of the disclosure encompasses embodiments of a method of detecting a cell or a population of cells expressing pyruvate kinase M2, said method comprising: (i) contacting a cell or population of cells with a pharmaceutically acceptable PET-detectable radiolabelled probe composition comprising at least one probe having a radionuclide and having the formula:

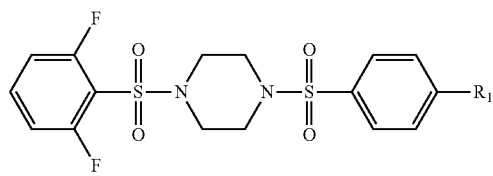

wherein $R_1$ is selected from the group consisting of: $^{11}$C-methoxy, $^{18}$F-fluoromethoxy-, $^{18}$F-fluoroethoxy-, and $^{18}$F-fluoromethoxy-; and (ii) detecting pyruvate kinase M2-specific binding of the radionuclide-containing probe within the cell or population of cells by detecting the presence of the radionuclide in the cell or population of cells.

In some embodiments of this aspect of the disclosure, the probe has the formula:

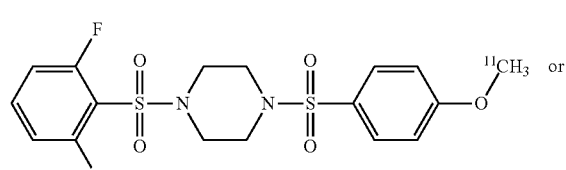

II

In some embodiments of this aspect of the disclosure, the method can further comprise the step of delivering the pharmaceutically acceptable probe composition to a human or non-human animal.

In some embodiments of this aspect of the disclosure, the step (ii), the detection of the radionuclide can be by Positron Emission Tomography (PET).

Yet another aspect of the disclosure encompasses embodiments of a method of detecting in a human or non-human animal a localized population of cells expressing pyruvate kinase M2 (PKM2), said method comprising the steps of: (i) administering to a human or non-human animal a pharmaceutically acceptable composition comprising a radiolabeled pyruvate kinase M2 (PKM2)-specific probe having the formula:

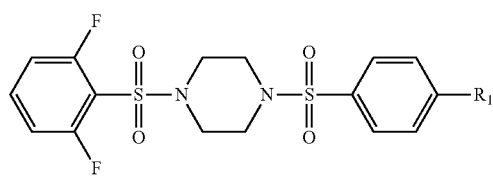

wherein $R_1$ is selected from the group consisting of: $^{11}$C-methoxy, $^{18}$F-fluoromethoxy-, $^{18}$F-fluoroethoxy-, and $^{18}$F-fluoromethoxy-; and (ii) identifying a tissue in the animal or human host wherein the amount of the detectable label in the tissue is greater than in other tissues of the host, thereby identifying a population of cancer cells expressing pyruvate kinase M2.

In some embodiments of this aspect of the disclosure, the probe has the formula:

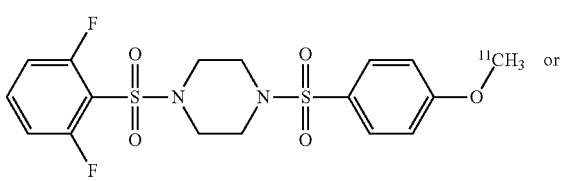

II

III

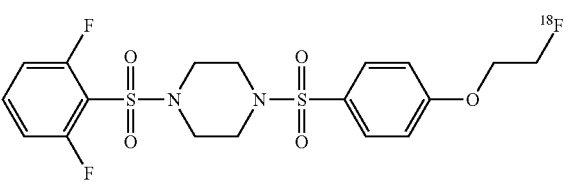

In some embodiments of this aspect of the disclosure, the radiolabeled pyruvate kinase M2 (PKM2)-specific probe is detected by Positron Emission Tomography (PET) scanning.

In some embodiments of this aspect of the disclosure, the tissue is a glioma of the brain.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Cell Culture: HeLa cells (ATCC) and U87 human glioma cells (ATCC) were grown in Dulbecco modified Eagle medium (DMEM; Life Technologies), containing 10% FBS, 2 mM L-glutamine and 2.5 mL penicillin/streptomycin (100 IU.mL$^{-1}$/100 mg.mL$^{-1}$).

GBM39 was transfected with a lentiviral vector that expressed a fusion protein of GFP and firefly luciferase. GBM39 cells were grown in a defined, serum-free medium consisting of a 1:1 mixture of Neurobasal-A Medium DMEM/F12 that also contained HEPES Buffer Solution (10 mM), MEM sodium pyruvate solution (1 mM), MEM non-essential amino acids solution 10 mM (1×), GlutaMAX-I Supplement (1×), and antibiotic-antimycotic (1×) from Life Technologies Inc. The full working medium was additionally supplemented with H-EGF (20 ng/mL), H-FGF-basic-154 (20 ng/mL), H-PDGF-AA (10 ng/mL), H-PDGF-BB (10 ng/mL), and heparin solution, 0.2% (2 μg/mL) as growth factors (all from Shenandoah Inc.) and B-27 (Life Technologies Inc.). All cells were incubated at 37° C. in a humidified atmosphere containing 5% $CO_2$.

Example 2

Cold Standard and Precursor Synthesis: The precursor for radiosynthesis was obtained through the reaction scheme illustrated in FIG. 9. 1-tert-butyloxycarbonyl(BOC)-piperazine 1 (1.34 mmol, 1 equiv.) was dissolved in dichloromethane (2.5 mL) under nitrogen and cooled to 0° C. Triethylamine (2.68 mmol, 2.0 equiv.) was added followed by portion-wise addition of 2,6-difluorobenzenesulfonyl chloride 2 (1.48 mmol, 1.1 equiv.). The reaction was stirred at 0° C. for 1 h and quenched with saturated aqueous ammonium chloride solution. The organic layer was washed with brine, dried over sodium sulfate, and concentrated in vacuo. The residue was purified via silica gel chromatography using a 95/5-5/95, hexane/EtOAc (v/v) gradient to give tert-butyl 4-((2,6 difluoro-phenyl)-sulfonyl)piperazine-1-carboxylate 3 as white crystals (80% yield).

BOC-protected compound 3 (1.04 mmol) was dissolved in dichloromethane (1 mL) and cooled to 0° C. Trifluoroacetic acid (TFA, 1 mL) was added, and the reaction was monitored by TLC. After the reaction was complete, the solvents were evaporated in vacuo to yield the TFA salt of compound 4 as a light yellow oil, which was carried onto the next step without further purification. The oily residue 4 was dissolved in dichloromethane (2 mL) and cooled to 0° C.

Triethylamine (4.16 mmol, 4 equiv.) was added followed by portion-wise addition of 4-hydroxybenzene-1-sulfonyl chloride (1.14 mmol, 1.1 equiv.). The progress of the reaction was monitored via thin-layer chromatography (TLC), and once complete, the reaction was quenched with saturated aqueous ammonium chloride solution (3 mL). The organic layer was washed twice with saturated ammonium chloride solution, once with brine, dried over sodium sulfate, and concentrated in vacuo. The resulting product was dissolved in DMSO and purified by RP-HPLC [Phenomenex Luna C18 column (5 μm, 10×250 mm), water/acetonitrile gradient (70:30-10:90 in 30 min) containing 0.1% TFA (v/v); the extinction at 240 nm was monitored for detection], to yield the pure phenolic precursor as white crystals (33% yield).

NMR spectra were acquired on a Varian Inova spectrometer operating at 300 MHz for $^1$H and are referenced internally according to residual solvent signals. Data for $^1$H NMR were recorded as follows: chemical shift (δ, ppm), multiplicity (s, singlet; d, doublet; t, triplet; m, multiplet; bs, broad singlet), integration, coupling constant (Hz).

Precursor:$^1$H NMR (CDCl$_3$, 300 MHz): δ (ppm)=7.661 (d, $^3J_{H,H}$=8.7 Hz, 2H), 7.574 (m, 1H), 7.075 (m, 2H), 6.987 (d, $^3J_{H,H}$=8.7 Hz, 2H), 5.648 (bs, 1H), 3.393 (m, 4H), 3.150 (m, 4H). MS (Cl) m/z: [M+H]$^+$ calculated for $C_{16}H_{16}F_2N_2O_5S_2$ 419.05; found 419.08.

DASA-23 was synthesized as a standard to confirm the identity of [$^{11}$C]DASA-23 using previously described methods (Boxer et al., (2010) J. Med. Chem. 53: 1048-1055; Israelsen et al., (2013) Cell 155: 397-409, incorporated herein by reference in its entirety). DASA-23: $^1$H NMR (CDCl$_3$, 300 MHz): δ (ppm)=7.685 (d, $^3J_{H,H}$=9.4 Hz, 2H), 7.563 (m, 1H), 7.057 (m, 4H), 3.921 (s, 3H), 3.392 (m, 4H), 3.151 (m, 4H).

Example 3

Radiosynthesis: Synthesis of [$^{11}$C]DASA-23 (FIGS. 2A and 9) was accomplished with a GE TRACERLab FX$_{C\ Pro}$ module by reacting 4-((4-((2,6-difluorophenyl)sulfonyl)piperazin-1-yl)sulfonyl)phenol (2.4 μmol) with [$^{11}$C]methyl triflate in acetonitrile (300 μL) for 3 min at 80° C., using 5

N NaOH (24 μmol) as base. The reaction mixture was diluted with 1 mL water and loaded on a semi-prep HPLC for purification (Phenomenex Luna C18 5μ, 250×10 mm, 50% acetonitrile, 50% 0.1 M $NH_4HCO_2$ with 0.5% AcOH; 7 mL/min). The fraction corresponding to [$^{11}$C]DASA-23 (retention time, $t_R$=9.5 min) was collected into a round flask preloaded with 20 mL water. The diluted aqueous fraction was passed through a pre-conditioned C-18 light Sep-Pak cartridge (Waters). The loaded cartridge was washed with sterile water (5 mL). [$^{11}$C]DASA-23 was eluted from the cartridge using ethanol (0.75 mL) and then saline (6.75 mL). The overall synthesis time was 52 min. Analytical HPLC (Phenomenex Gemini C18 5μ, 250×4.6 mm, 60% acetonitrile, 40% 0.1 M $NH_4HCO_2$ with 0.5% AcOH, 1 mL/min) was used for assessment of radiochemical purity and specific activity.

Example 4

Cell Uptake and Efflux Studies: U87 and HeLa cells ($2\times10^5$) were plated into 6-well plates overnight before [$^{11}$C]DASA-23 uptake analysis. On the day of the experiment, fresh, pre-warmed DMEM containing 0.925 MBq of [$^{11}$C]DASA-23 was added to individual wells (1 mL/well, 9.25±4.63 pmol).

Cells were incubated with [$^{11}$C]DASA-23 at 37° C. and 5% $CO_2$ over a 60 min time course. At the respective time points, plates were placed on ice, washed 3 times with ice-cold phosphate-buffered saline (PBS), and lysed in radioimmunoprecipitation assay buffer (Thermo Fisher Scientific Inc.; 500 μL). 300 μL cell lysates were transferred to counting tubes and decay-corrected radioactivity was determined on a y counter (Cobra II Auto-Gamma counter; Packard Biosciences Co.). The remaining lysate was frozen and used following radioactive decay for protein determination using a bicinchoninic acid (BCA) 96-well plate assay (Thermo Fisher Scientific Inc.) and for immunoblotting. In addition, 10 μL standards from the 0.925 MBq/mL solution added to cells were counted to quantitate percentage radiotracer uptake. For efflux studies, cells were incubated with radiotracer for 60 min, washed 3 times with room temperature (RT) Hank's Buffered Salt Solution (HBSS) before subsequent incubation at 37° C. in fresh, radiotracer-free, DMEM. At allotted times, samples were processed.

Example 5

PKM2 siRNA: Time course PKM2 knockdown in HeLa cells was assessed over 72 h post-transfection. Cells were seeded in 6-well plates in antibiotic-free DMEM at $1.5\times10^6$ cells/well 24 h prior to siRNA transfection with DharmaFECT1 (Thermo Scientific), according to the manufacturer's instruction. Specific siRNA targeting only PKM2 were custom made by Thermo Scientific using the following sequences: CCAUAAUCGUCCUCACCAAUU (sense) (SEQ ID NO: 1), UUGGUGAGGACGAUUAUGGUU (antisense) (SEQ ID NO: 2). Scrambled siRNA (siCtrl; Cell Signaling Technology) was used as a control. siRNA were added at a final concentration of 25 nM. [$^{11}$C]DASA-23 uptake (0.925 MBq/mL) was measured after 30 min in cells transfected with siCtrl and siPKM2 at 24 h, 48 h and 72 h post transfection, and processed as described in Example 4, above. Untreated cells were used as a further control, measured 24 h post addition of fresh DMEM and 96 h post seeding.

Example 6

Western Blotting: Monoclonal rabbit antibody to PKM1 and PKM2 (1:1000 dilution, Cell Signaling Technology) were used in a standard western blotting protocol. A rabbit anti-actin antibody (Sigma-Aldrich Co. Ltd; 1:2000) was used as a loading control. Blots were scanned and signal quantification was performed using ImageJ (National Institutes of Health).

Example 7

In vivo Tumor Models: For subcutaneous tumor models, U87 tumor cells ($5\times10^6$ cells; 100 μL PBS) were injected subcutaneously on the back of female BALB/c nude mice (aged 6-8 weeks; Charles River Laboratories) and grown to approximately 150 $mm^3$. Tumor dimensions were measured periodically using a caliper (by the same experienced researcher), with tumor volumes calculated by the equation: volume=$(\pi/6) \times a \times b \times c$, where a, b, and c represent three orthogonal axes of the tumor. For orthotopic brain tumor models, $2\times10^5$ U87 cells were implanted 0.5 mm anterior and 2 mm to the right of the bregma in the brains of 6-8 week-old nude mice, held in place using a stereotactic unit. The cells, suspended in 4 μL PBS, were injected at a depth of 3 mm over 5 min with an AS blunt-ended Hamilton syringe, which was subsequently held in place for a further 5 min. Animals were anaesthetized with an i.p. injection of 150 mg/kg ketamine, 15 mg/kg xylazine. Mice were subsequently imaged by MRI and PET 32-35 days post intracranial injection and GBM39 tumor-bearing mice were imaged between 44-50 days after implantation. For blocking studies, mice were imaged with [$^{11}$C]DASA-23 at baseline and then 24 hours later with a second tail-vein injection of [$^{11}$C]DASA-23, 1 hour after i.p. injection of TEPP-46 [50 mg/kg in 40% w/v (2-hydroxypropyl)-β-cyclodextrin in water; about 3 μmol; Cayman Chemical].

Example 8

Imaging Studies: MRI was performed in an actively-shielded Discovery MR901 General Electric 7T horizontal bore scanner (GE Healthcare) including Integrated Electronics Company (IECO) gradient drivers, an Agilent 120 mm inner diameter shielded gradient insert (600 mT/m, 1000 T/m/s), EXCITE2 electronics; the supporting LX11 platform; and a 3 cm inner diameter Millipede quadrature transmit/receive volume RF coil. Animals were anesthetized with 2% isoflurane in oxygen, and physiological monitoring included respiration, and temperature feedback for surface body temperature maintenance by warm airflow over the animal. A fast spoiled gradient echo (FSPGR) sequence (TR=9.7 ms; TE=2.1 ms; flip angle=5°; NEX=20; FOV=2 cm; image matrix=160×160; slice thickness=1 mm) was used to acquire 3 sets of 12, 12, and 8 orthogonal $T_1$-weighted images in the axial, sagittal, and coronal planes through the mass, respectively. PET-MR registration was performed in IRW (Siemens) using the CT image for alignment of the skull.

PET imaging scans were carried out on a docked Siemens Inveon PET/CT scanner (matrix size, 128×128×159; CT attenuation-corrected; non-scatter corrected), following a bolus i.v. injection of approximately 18.5 MBq of [$^{11}$C]DASA-23 into tumor-bearing mice. Dynamic scans were acquired in list mode format over 60 min. The acquired data were then sorted into 0.5-mm sinogram bins and 19 time frames for image reconstruction (4×15 s, 4×60 s and 11×300 s), which was done by iterative reconstruction using the following parameters: 3D ordered-subsets expectation maximization (3D-OSEM) followed by fast maximum a posteriori (fastMAP); MAP OSEM interations, 2; MAP subsets, 16; MAP iterations, 18.

The count densities were averaged for all volumes of interest at each time point to obtain a time versus radioactivity curve (TAC). Tumor and tissue TACs were normalized to injected dose, measured by a CRC-15 PET dose calibrator (Capintec, Inc.), and expressed as percentage injected dose per milliliter of tissue (% ID/mL). The area under the TAC, calculated as the integral of % ID/mL from 0 to 60 min, and the normalized uptake of radiotracer at 60 min (% ID/mL$_{60}$) were also used for comparisons. Siemens Inveon Research Workplace software (v.4.0) was used for visualization of radiotracer uptake in the tumor, to define the three-dimensional (3D) volumes of interest (VOI) and for 3D-visualization to create volume rendering technique (VRT) images.

Example 9

Ex vivo Biodistribution: After the PET imaging studies, 60 min post radiotracer administration, mice were sacrificed by exsanguination via cardiac puncture and tissues harvested. Tissue radioactivity for all organs was subsequently determined on a gamma counter (decay-corrected; Cobra II Auto-Gamma counter, Packard Biosciences Co, Pangbourne, UK). Ten-microliter standards from the stock activity were also counted for data normalization. Data were expressed as percent injected dose per gram of tissue (% ID/g).

Example 10

Ex vivo Autoradiography: Autoradiography was performed as described in James et al., ((2012) *J. Med. Chem.* 55: 8272-8282, incorporated herein by reference in its entirety). In brief, coronal brain sections of U87 and GBM39 tumor-bearing mice were obtained 20 min after i.v. injection of 26 MBq [$^{11}$C]DASA-23. Anesthetized mice were perfused with saline (10 mL) to remove intravascular [$^{11}$C]DASA-23, and after cervical dislocation, the brain was removed and embedded in optimal cutting temperature (OCT) compound (Tissue-Tek) before being frozen on dry ice. Subsequently, 10 µm thick coronal brain sections were cut with a cryostat microtome HM500 (Microm). The sections were mounted on microscope slides (Fisherbrand Superfrost Plus microscope slides), air-dried for a minimum of 5 min, and then exposed to MultiSensitive storage phosphor screens (Perkin-Elmer) for 3 hours at −20° C. The image plates were analyzed with a Typhoon 9410 variable mode imager (Amersham Biosciences), and image data were visualized and processed by Image J.

Example 11

Plasma Stability: [$^{11}$C]DASA-23 stability in mouse plasma was assessed ex vivo according to previously described methodology (James et al., (2012) *J. Med. Chem.* 55: 8272-8282, incorporated herein by reference in its entirety).

Samples were incubated for 10 min, 30 min, and 60 min and compared to a standard from the respective injected probe.

Example 12

Histopathology: Following imaging, anaesthetized mice bearing orthotopically-implanted U87 tumors were transcardially perfused with 0.9% saline, followed by the removal of the brain. Formalin-fixed brains (10% v/v) were embedded in paraffin, horizontally sectioned into 5 µm-thick slices and mounted on microscope slides according to standard procedures (Histo-Tec laboratory). Sections were taken at regular intervals across the entire brain. Every sixth section was stained with hematoxylin and eosin (H&E; Histo-Tec laboratory). Immunohistochemistry against human PKM1 and PKM2 using a rabbit anti-human monoclonal antibody (Cell Signaling Technology; 1:100) was performed on paraffin-embedded sections using standard techniques and according to the manufacturer's instructions (Cell Signaling Technology) (as shown in FIGS. 7A-7C). Prior to staining, antigen retrieval was performed in 10 mM sodium citrate buffer at 90° C. for 10 min. For detection, VECTASTAIN Elite ABC and Vector NovaRED (Vector Laboratories) were used per manufacturer's recommendations.

Example 13

Six to seven animals per group were used for the evaluation of PKM2 in orthotopic models of GBM, calculated with 90% power and a 5% significance level. For TEPP-46 treatment studies, animals were randomized before imaging and subsequent treatment. All outliers were included in the analysis and no data were excluded. Researchers were not blinded to the results. A minimum of 3 experimental replicates were recorded for all in vitro data.

Statistical Analysis: Data were expressed as mean±SD. Statistical significance was determined using a two-tailed Student's t test. Paired t tests were used for longitudinal studies (FIG. 8E), with unpaired t tests used to derive significance for all other analyses. For the analysis of [$^{11}$C]DASA-23 uptake in multiple tissues, significance was determined by ANOVA, followed by Tukey's honest significant difference test. Correlation analysis using Spearman's rank correlation, linear regression, statistical significance, and 95% confidence levels were determined using Prism software for Mac OSX (v.6.0e; GraphPad Software). Differences between groups were considered significant if P≤0.05.

Example 14

[$^{11}$C]DASA-23 is Rapidly Taken up by Tumor Cells: DASA-23 was labeled at its aromatic methoxy moiety with $^{11}$C ($t_{1/2}$=20.4 min) from the corresponding nor-derivative of DASA-23 and the highly efficient methylation reagent [$^{11}$C]CH$_3$OTf (as shown in the schema of FIG. 2A), with a radiochemical yield of 2.4±0.8%, >99% radiochemical purity, and a specific activity of 159.2±94.3 GBq/µmol at the end of synthesis (EOS; n=12). The identity of the radiochemistry precursor and cold standard was confirmed through mass spectrometry and nuclear magnetic resonance (NMR) spectroscopy, and the identity of the radiotracer ([$^{11}$C]DASA-23) was confirmed by high performance liquid chromatography (HPLC) via co-injection with cold standard.

Addition of [$^{11}$C]DASA-23 resulted in rapid and extensive cellular uptake and retention in both HeLa and U87 tumor cells, reaching 14.9±2.0%radioactivity/mg protein and 19.6±2.0% radioactivity/mg protein, respectively by 30 min (FIGS. 2B and 2C, left-hand panes). Removal of exogenous radioactivity resulted in efflux of cell-associated activity, with about 40% of the initial intracellular radioactivity retained 30 min post removal of exogenous [$^{11}$C] DASA-23 for both cell lines (FIGS. 2B and 2C, right-hand panels).

Example 15

Retention of [$^{11}$C]DASA-23 is Closely Correlated to PKM2 Expression: To determine the specificity of [$^{11}$C] DASA-23 to annotate PKM2 expression in cancer cells, small inhibitory RNA (siRNA) was used to modulate PKM2 protein expression in culture. Knockdown of PKM2 was observed by 48 h post transfection, with nearly complete protein ablation detected by 72 h (FIG. 3A). Extended incubation in culture medium in the presence of scrambled, non-targeting siRNA (siCtrl) induced a temporal increase in PKM2 protein expression. Low levels of PKM1 were measured in naïve cells, with no change in PKM1 expression detected 72 h post transfection with either siPKM2 or siCtrl.

Next, cell uptake of [$^{11}$C]DASA-23 was compared to protein levels of PKM2. A significant 16.5% reduction in [$^{11}$C]DASA-23 uptake was measured in siPKM2 cells versus those transfected with control siRNA just 24 h post transfection (P=0.011; n=3). By 72 h [$^{11}$C]DASA-23 uptake in siPKM2 cells was reduced to 44.5% of siCtrl cells (P<0.001; n=3; FIG. 3B). [$^{11}$C]DASA-23 strongly correlated with PKM2 protein expression, determined from analysis of the same cell lysates ($R^2$=0.828), albeit with some non-specific cell retention in cells with low PKM2 expression (FIG. 3C).

Example 16

[$^{11}$C]DASA-23 Characteristics for in vivo Tumor Imaging: Given the favorable tumor cell retention and specificity of [$^{11}$C]DASA-23 in culture, small animal [$^{11}$C]DASA-23-PET in a nude mouse model implanted with subcutaneous (s.c.) U87 human glioma xenografts were examined. [$^{11}$C] DASA-23 radiotracer distribution was characterized by liver uptake and clearance through both renal and hepatobiliary routes, accompanied by good tumor accumulation (FIG. 4A).

Ex vivo biodistribution studies corroborated the PET imaging data (FIG. 4B). Of note, [$^{11}$C]DASA-23 did not accumulate in the brain. 60 min post [$^{11}$C]DASA-23 injection, U87 tumor uptake was 1.78±0.23% of the injected dose (ID)/g (n=4 animals). At this time point, the uptake ratios of U87 tumor to blood, muscle and brain were 1.1, 1.6 and 2.1 respectively. Additionally, [$^{11}$C]DASA-23 showed excellent stability in plasma, with >96% of parent remaining after 60 min (FIG. 4C).

Dynamic [$^{11}$C]DASA-23 PET imaging confirmed rapid liver and kidney uptake, followed by clearance through the bladder and small intestine (FIGS. 5A and 5B). Rapid tumor uptake of [$^{11}$C]DASA-23, peaking at 10 minutes, proceeded a slow washout of radioactivity over the remaining 50 minutes (FIG. 5C). Muscle uptake of [$^{11}$C]DASA-23 followed a similar pattern of retention but at lower levels. This was contrasted with [$^{11}$C]DASA-23 uptake in the brain, where high initial delivery, peaking 30 s after injection, was followed by rapid clearance, reaching background levels by 10 min post injection.

Example 17

[$^{11}$C]DASA-23 Accumulates in Orthotopically-growing U87 Tumors: The ability of [$^{11}$C]DASA-23 to image orthotopically grown U87 tumors was explored. MicroPET after i.v. injection of [$^{11}$C]DASA-23 clearly allowed the detection of intracerebral tumors, shown in the fused PET-CT images, as shown, for example, in FIG. 6A. Similarly to subcutaneous xenograft tumors, U87 tumor kinetics were characterized by rapid initial uptake preceding slow washout. In comparison, radioactivity from the control, contralateral, region of the brain reached similar levels of radiotracer delivery (P>0.05; FIG. 18), but it was not retained (FIG. 6B).

Time course images of initial [$^{11}$C]DASA-23 uptake in the healthy brain and subsequent retention in orthotopic U87 tumors are shown in FIG. 17. By 30 min after injection, [$^{11}$C]DASA-23 radioactivity in the tumor was 1.68±0.47% ID/g versus 0.78±0.18% ID/g in the contralateral background tissue (n=6; P=0.003). To confirm that the PET signal corresponded with orthotopically-growing tumors, we performed contrast-enhanced MRI was performed on the same animals (FIG. 6C) and co-registered these with the [$^{11}$C]DASA-23-PET images (FIG. 6D). Contrast-enhancing U87 tumors, clearly defined in the $T_1$-weighted images, excellently matched the corresponding microPET images. The trace amount of [$^{11}$C]DASA-23 (approximately 200 pmol) used here was about 15,000× lower than the amount used in previous drug studies (approximately 3 μmol) such as reported by Anastasiou et al., *Nat. Chem. Biol.* 8: 839-847.

Following imaging, the brains of tumor-bearing mice were excised for analysis by histopathology. H&E staining confirmed excellent correlation of PET signal intensity with histopathological findings (FIGS. 7A-7C). The PET signal of orthotopic U87 tumors was sharply delineated from the surrounding brain tissue (FIG. 6D), matching the pattern of cytosolic PKM2 expression shown in tissue sections (FIG. 7B, and FIG. 17). PKM1 expression was exclusively located in the normal healthy brain and absent from intracranial tumors (FIG. 7C). At higher magnifications (10×; FIGS. 7A-7C, right-hand panels), U87 tumor cells infiltrating away from the margins of the primary tumor were clearly delineated through the presence of PKM2 and absence of PKM1. Localization of [$^{11}$C]DASA-23 to small (approximately 1 mm diameter) intracranial PKM2-positive tumors was shown through ex vivo autoradiography (FIG. 18). Together, these data highlight the ability for [$^{11}$C]DASA-23-PET to clearly detect orthotopically growing human gliomas through measurement of tumor-specific PKM2 expression.

Example 18

[$^{18}$F]FE-PKM2 Passes the Blood Brain Barrier: In vivo imaging of non-tumor bearing mice with [$^{18}$F]FE-PKM2 (III) demonstrated high normal brain uptake soon after injection (FIG. 13, left two panels), proceeded by rapid washout over the remaining imaging time course (FIG. 13, right two panels, and FIG. 14).

Example 19

[$^{11}$C]DASA-23 shows Utility as a PKM2 Companion Diagnostic in Patient-derived Intracranial Tumors: Patient-derived xenograft (PDX) models are enhanced preclinical tools that better represent human tumor biology and patient response to therapy (Hidalgo et al., (2014) *Cancer Discov.* 4: 998-1013). To test whether [$^{11}$C]DASA-23-PET could image these more clinically relevant tumors, GBM39 PDXs were implanted orthotopically in the brains of nude mice and monitored their growth via bioluminescence imaging (BLI). By 50 days after implantation, a strong BLI signal originating from the head of GBM39 tumor-bearing mice was evident (FIG. 8A). Mice were subsequently imaged with [11C]DASA-23, which clearly identified the intracerebral tumors (FIG. 8B), appearing as distinct regions of infiltrative growth (FIG. 8C).

Having previously demonstrated the specificity of [11C] DASA-23 for the detection of PKM2 in cell culture (FIGS. 3A-3C), it was determined whether the PET signal originating from the intracranial tumors in vivo corresponded to tumor-specific PKM2 expression. The short half-life of carbon-11 permitted the use of the same mice in longitudinal studies, where [11C]DASA-23 tumor uptake was assessed at baseline and subsequently after challenge with a blocking agent, 24 hours after initial evaluation. A structurally distinct PKM2 activator, TEPP-46, a highly selective PKM2 activator which binds with nanomolar affinity (Jiang et al., (2010) Bioorg. Med. Chem. Lett. 20: 3387-3393), was selected to test the specificity of [11C]DASA-23 for PKM2. One hour after TEPP-46 injection, animals were reimaged with [11C]DASA-23, which revealed complete ablation of tumor signal to background levels present in the healthy contralateral regions of the brain (FIGS. 8B and 8C). This was expected because DASA-23 and TEPP-46 share the same PKM2 binding pocket, with TEPP-46-bound PKM2 made inaccessible for [11C]DASA-23 binding and retention in tissues. Of interest was the reduction of retention of [11C]DASA-23 in the harderian glands (FIG. 8C), likely indicating PKM2 expression in this tissue. Contrast-enhanced MRI performed at the end of the study confirmed the presence of enhancing infiltrative tumors (FIG. 8D), with tumor-associated [11C]DASA-23 retention 30 min after radiotracer injection reduced from 1.61±0.25% ID/g at baseline to 0.93±0.10% ID/g after TEPP-46, a 42% decrease (P=0.0009; n=7; FIG. 6E). The uptake in control, contralateral healthy brain was 0.79±0.18% ID/g (P=0.10). As with U87 tumors, autoradiography of excised GBM39-containing brains revealed precise localization of radioactivity to small PKM2-expressing tumors (FIGS. 8D and 8E).

What is claimed:

1. A pyruvate kinase M2 activator precursor wherein said precursor is 4-((4-((2,6-difluorophenyl)sulfonyl)piperazin-1-yl)sulfonyl)phenol (I) having the formula:

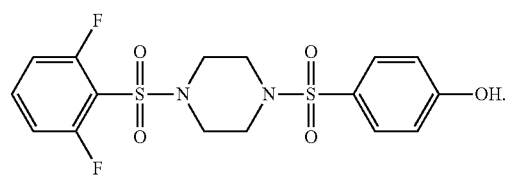

2. A method of generating a pyruvate kinase M2 activator precursor, wherein said precursor is 4-((4-((2,6-difluorophenyl)sulfonyl)piperazin-1-yl)sulfonyl)phenol (I) and, wherein said method is according to scheme A:

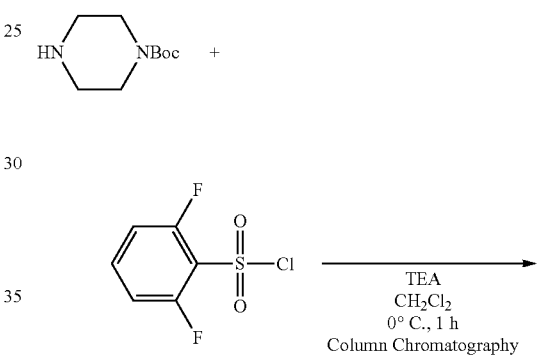

Scheme A.

---

SEQUENCE LISTING

<160> NUMBER OF SEQ ID NOS: 2

<210> SEQ ID NO 1
<211> LENGTH: 21
<212> TYPE: RNA
<213> ORGANISM: Artificial sequence
<220> FEATURE:
<223> OTHER INFORMATION: Pyruvate Kinase M2-specific sense siRNA

<400> SEQUENCE: 1
ccauaaucgu ccucaccaau u       21

<210> SEQ ID NO 2
<211> LENGTH: 21
<212> TYPE: RNA
<213> ORGANISM: Artificial sequence
<220> FEATURE:
<223> OTHER INFORMATION: Pyruvate kinase M2-specific antisense siRNA

<400> SEQUENCE: 2
uuggugagga cgauuauggu u       21

-continued

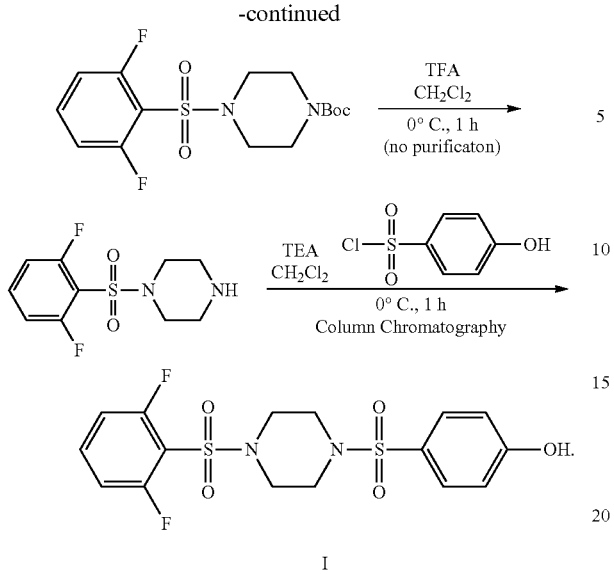

3. A pharmaceutically acceptable probe composition comprising a Positron Emission Tomography (PET)-detectable radiolabelled probe, wherein said probe has the formula:

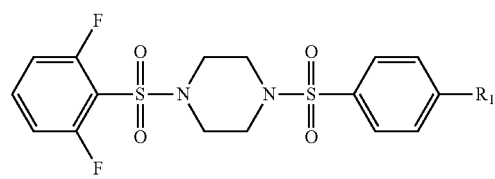

wherein $R_1$ is selected from the group consisting of: $^{11}$C-methoxy, $^{18}$F-fluoromethoxy-, $^{18}$F-fluoroethoxy-, and $^{18}$F-fluoropropoxy-.

4. The pharmaceutically acceptable probe composition according to claim 1 wherein said probe has the formula:

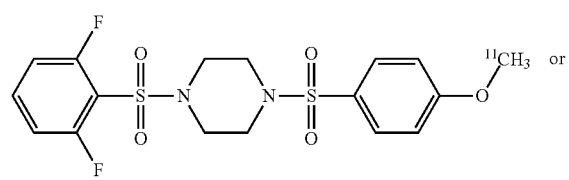

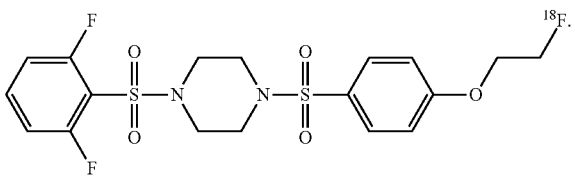

5. The pharmaceutically acceptable probe composition of claim 3 further comprising a pharmaceutically acceptable carrier.

6. A method of generating a radiolabelled probe, wherein said method is according to scheme B:

Scheme B

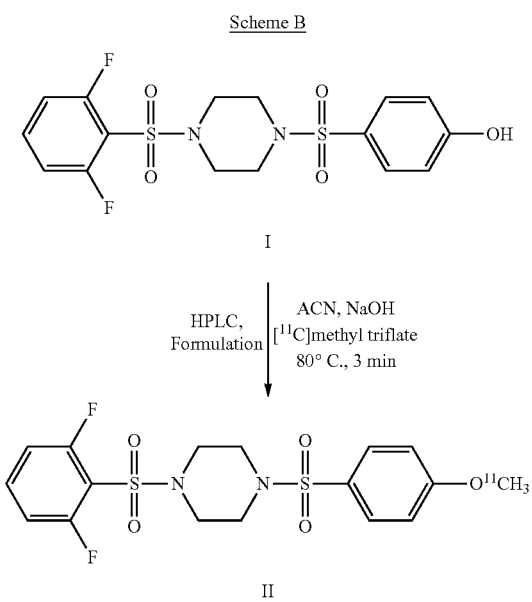

or according to scheme C:

Scheme C

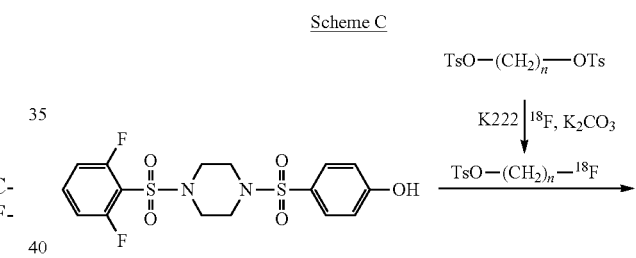

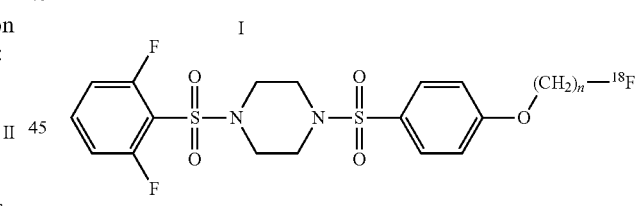

wherein n is 1, 2, or 3.

7. A method of detecting a cell or a population of cells expressing pyruvate kinase M2, said method comprising:
(i) contacting a cell or population of cells with a pharmaceutically acceptable PET-detectable radiolabelled probe composition comprising at least one probe having a radionuclide and having the formula:

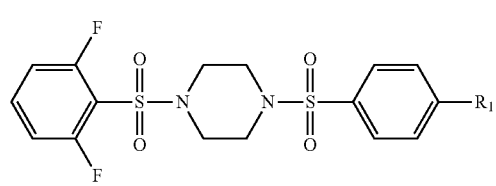

wherein $R_1$ is selected from the group consisting of: $^{11}$C-methoxy, $^{18}$F-fluoromethoxy-, $^{18}$F-fluoroethoxy-, and $^{18}$F-fluoromethoxy-; and (ii) detecting pyruvate kinase M2-specific binding of the radionuclide-containing probe within the cell or population of cells by detecting the presence of the radionuclide in the cell or population of cells.

8. The method of claim 7, wherein the probe has the formula:

II

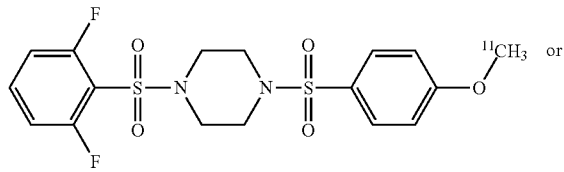

or

III

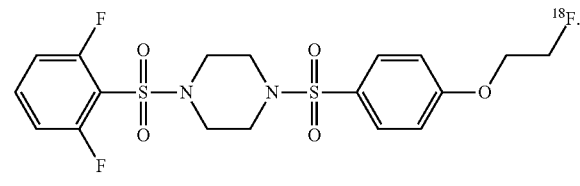

9. The method of claim 7, further comprising the step of delivering the pharmaceutically acceptable probe composition to a human or non-human animal.

10. The method of claim 7, wherein in step (ii), the detection of the radionuclide is by Positron Emission Tomography (PET).

11. A method of detecting in a human or non-human animal a localized population of cancer cells expressing pyruvate kinase M2 (PKM2), said method comprising the steps of:

(i) administering to a human or non-human animal a pharmaceutically acceptable composition comprising a radiolabeled pyruvate kinase M2 (PKM2)-specific probe having the formula:

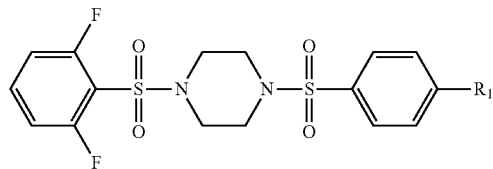

wherein $R_1$ is selected from the group consisting of: $^{11}$C-methoxy, $^{18}$F-fluoromethoxy-, $^{18}$F-fluoroethoxy-, and $^{18}$F-fluoromethoxy-; and (ii) identifying a tissue in the animal or human host, wherein the amount of the detectable label in the tissue is greater than in other tissues of the host, thereby identifying a population of cancer cells expressing pyruvate kinase M2.

12. The method of claim 11, wherein the probe has the formula:

II

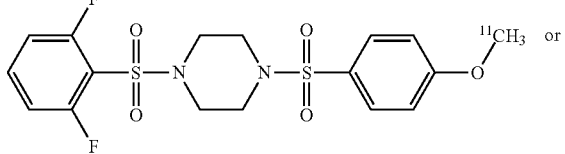

or

III

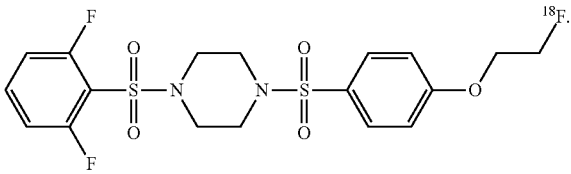

13. The method of claim 11, wherein the radiolabeled pyruvate kinase M2 (PKM2)-specific probe is detected by Positron Emission Tomography (PET) scanning.

14. The method of claim 11, wherein the tissue is a glioma of the brain.

* * * * *